United States Patent
Paidi et al.

(10) Patent No.: US 10,254,249 B2
(45) Date of Patent: Apr. 9, 2019

(54) METHOD OF MAGNETIC ANALYSIS TO DETERMINE THE CATALYTIC ACTIVITY OF METAL OXIDES INCLUDING NANOCERIA

(71) Applicants: The University of Manitoba, Winnipeg (CA); Toyota Motor Engineering & Manufacturing North America, Inc., Erlanger, KY (US)

(72) Inventors: Vinod K. Paidi, Winnipeg (CA); Johan A. Van Lierop, Winnipeg (CA); Charles A. Roberts, Farmington Hills, MI (US)

(73) Assignees: The University of Manitoba, Winnipeg (CA); Toyota Motor Engineering & Manufacturing North America, Inc., Erlanger, KY (US)

(*) Notice: Subject to any disclaimer, the term of this patent is extended or adjusted under 35 U.S.C. 154(b) by 85 days.

(21) Appl. No.: 15/646,863

(22) Filed: Jul. 11, 2017

(65) Prior Publication Data
US 2019/0017964 A1    Jan. 17, 2019

(51) Int. Cl.
*B01J 23/10*   (2006.01)
*G01N 27/72*   (2006.01)
*G01R 33/16*   (2006.01)

(52) U.S. Cl.
CPC ............. *G01N 27/72* (2013.01); *B01J 23/10* (2013.01); *G01R 33/16* (2013.01)

(58) Field of Classification Search
CPC ................................. G01N 27/72; G01R 33/16
See application file for complete search history.

(56) References Cited

U.S. PATENT DOCUMENTS 7,504,356 B1    3/2009    Self et al.
8,968,667 B2    3/2015    Princivalle et al.
(Continued)

OTHER PUBLICATIONS

Ahmidou Laachir, et al., "Reduction of $CeO_2$ by Hydrogen. Magnetic Susceptibility and Fourier-Transform Infrared, Ultraviolet and X-Ray Photoelectron Spectroscopy Measurements" J. Chem. Soc., Faraday Trans. vol. 87, 1991, pp. 1601-1609.
(Continued)

Primary Examiner — Noam Reisner
(74) Attorney, Agent, or Firm — Oblon, McClelland, Maier & Neustadt, L.L.P.

(57) ABSTRACT

A method to predict the catalytic activity of a metal oxide of formula $M_xO_y$, where x is a number from 1 to 3 and y is a number from 1 to 8 is provided. The metal of the metal oxide has redox coupled oxidation states wherein the redox transformation is between oxidation states selected from the group consisting of a diamagnetic oxidation state ($M^{d+}$) and a paramagnetic oxidation state ($M^{p+}$), a paramagnetic oxidation state ($M^{p+}$) and a ferromagnetic oxidation state ($M^{f+}$), and a paramagnetic oxidation state ($M^{p+}$) and an antiferromagnetic oxidation state ($M^{a+}$) where d, p, f and a are independently numbers from 1 to 6 and one of the oxidation states ($M^{d+}$), ($M^{p+}$), ($M^{f+}$), and ($M^{a+}$) is formed by reduction by the $O^{2-}$. The magnetic susceptibility of the metal oxide as a sample in an oxygen environment at a specified temperature is correlated with a value of ($M^{d+}$ or $M^{p+}$ or $M^{f+}$ or $M^{a+}$)/g ($O_2$ rich). Then the magnetic susceptibility of the metal oxide as a sample in an oxygen free environment at the specified temperature is measured and correlated with a value of number of ($M^{d+}$ or $M^{p+}$ or $M^{f+}$ or $M^{a+}$)/g ($O_2$ deficient). The catalytic activity is predicted based on the difference of these two numbers.

4 Claims, 43 Drawing Sheets

(56) References Cited

U.S. PATENT DOCUMENTS

| | | |
|---|---|---|
| 9,023,550 B2 | 5/2015 | Brinkman |
| 9,101,916 B2 | 8/2015 | Princivalle et al. |
| 2006/0059877 A1 | 3/2006 | Yoshida |
| 2010/0148111 A1 | 6/2010 | Fuertes Miquel et al. |
| 2013/0052708 A1 | 2/2013 | Cheung et al. |
| 2013/0123100 A1 | 5/2013 | Cheung et al. |
| 2013/0136676 A1* | 5/2013 | Princivalle ......... B01D 53/8628 423/213.2 |

OTHER PUBLICATIONS

P. Dutta, et al. "Concentration of $Ce^{3+}$ and Oxygen Vacancies in Cerium Oxide Nanoparticles" Chem. Mater., vol. 18, No. 21, 2006, pp. 5144-5146.

Michael Nolan, et al., "Density Functional Theory Studies of the Structure and Electronic Structure of Pure and Defective Low Index Surfaces of Ceria" Surface Science, vol. 576, 2005, pp. 217-229.

Stephen Gregory, "Adsorbed Oxygen as an Amorphous Antiferromagnetic System" Physical Review Letters, vol. 39, No. 16, Oct. 17, 1977, pp. 1035-1038.

D. D. Awschalom, et al., "Melting and Wetting Behavior in Oxygen Films" Physical Review Letters, vol. 51, No. 7, Aug. 15, 1983, pp. 586-588.

U. Köbler, et al., "Susceptibility Study of Physisorbed Oxygen Layers on Graphite" Physical Review B., vol. 35, No. 18, Jun. 15, 1987, pp. 9809-9816.

Youichi Murakami, "Magnetic and Structural Phase Transitions of Physisorbed Oxygen Layers" J. Phys. Chem. Solids, vol. 59, 1998, pp. 467-485.

Alessandro Trovarelli, et al., "Nanophase Fluorite-Structured $CeO_2$—$ZrO_2$ Catalysts Prepared by High-Energy Mechanical Milling" Journal of Catalysis vol. 169, 1997, pp. 490-502.

\* cited by examiner

METHOD OF MAGNETIC ANALYSIS TO DETERMINE THE CATALYTIC ACTIVITY OF METAL OXIDES INCLUDING NANOCERIA

BACKGROUND

Field of the Disclosure

Transition metal oxides and oxides of the Lanthanide and Actinide metals are of interest as catalysts for numerous chemical reactions. Throughout this discussion unless specified differently, the term "metal oxide" will be understood to generically encompass, transition metal oxides, lanthanide metal oxides and actinide metal oxides. The members of these series may characteristically exist in at least two different oxidation states in the metal oxide lattice structure and redox interconversion of these different oxidation states is conventionally believed to explain or contribute to catalytic activity. Moreover, in the metal oxide matrix or crystal lattice the metal ion may be in coordination with from two to eight oxide ($O^{2-}$) ions and in consideration that the oxygen ions may serve as reducing agents to reduce the metal from a higher oxidation number to a lower oxidation number, the oxidation product from the $O^{2-}$ ion is molecular oxygen ($O_2$) which may vacate the lattice position occupied by the $O^{2-}$, becoming adsorbed oxygen which may then exit the lattice to an environment external to the lattice. As a result of this series of events a vacancy will be formed in the lattice at the position originally occupied by the $O^{2-}$. The presence of such oxygen vacancies and reduced metal ion may be categorized as lattice defects or simply defects.

A wide variety of methods to explain, understand and ultimately predict the catalytic activity of the metal oxides have been reported. However, to date, a method having universal utility has not been described.

Nanoscale $CeO_2$ (nanoceria) as a metal oxide is a versatile, commercially valuable catalytic material having redox properties which can be tuned by choice of method of preparation, particle size, dopant selection, particle shape and surface chemistry. Cerium in a fluorite crystal lattice may exist as a $Ce^{4+}$ oxidation state or a $Ce^{3+}$ oxidation state and this characteristic makes possible the formation of oxygen vacancies in the crystal lattice which may be the basis for a unique oxygen buffering capability as well as a capability to participate in both oxidation and reduction reactions. These properties may serve as the basis for the catalytic reactivity of nanoceria and utilization, for example, in catalytic converters, as diesel oxidation catalysts, intermediate temperature solid oxide fuel cells and sensors.

Oxygen vacancy defects in nanoceria and in metal oxides as described above are of special importance because of their impact on the structure and electronic properties of the surface and additionally, the $Ce^{4+}$ to $Ce^{3+}$ or appropriate metal redox cycles through oxygen vacancy formation. One important aspect of nanoceria's catalytic activity is its oxygen partial pressure dependent ability to undergo repeatable $Ce^{4+}$ to $Ce^{3+}$ redox cycles through oxygen vacancy formation. Oxygen vacancy transport, i.e. mobility of oxygen in the fluorite lattice, is therefore of fundamental interest due to the reactivity of these vacancies once they reach the crystal surface. Thus, discovery of a method to identify and quantify these vacancies or defects may be of universal utility for metal oxides.

The crystallographic defect structure of nanoceria is predominately oxygen vacancy based, where an oxygen ion is removed from a lattice position and a vacancy is created. The crystal structure of ceria is shown in FIG. 10 where each Ce ion (white sphere) is surrounded by eight $O^{2-}$ ions (black), and each $O^{2-}$ ion is surrounded by four Ce ions. The defect formation may be explained by the reaction:

$$4Ce^{4+}+O^{2-} \rightarrow 4Ce^{4+}+2e-/\square+1/2O_2 \rightarrow 2Ce^{4+}+2Ce^{3+}+\square+1/2O_2$$

where $\square$ is an oxygen vacancy and $O^{2-}$ and $O_2$ represent lattice and molecular oxygen, respectively[1]. This transformation is shown in FIG. 1. The $Ce^{4+}$ to $Ce^{3+}$ transformation is due to oxygen vacancy formation and the released oxygen in the fluorite lattice is intrinsic oxygen. The valence change of $Ce^{4+}$ to $Ce^{3+}$ with concomitant oxygen vacancy formation significantly modifies the reactivity of nanoceria. Esch et al.[2] proposed that these oxygen vacancies cluster and expose the $Ce^{3+}$ ions to gas phase reactants such as CO and NO. Campbell et al.[3] specifically reported that reactive $Ce^{3+}$ are formed when three oxygen ions are removed. Much of the interest in ceria materials is because of its high oxygen storage capacity from being able to rapidly form and eliminate these oxygen vacancies. Improvement of the catalytic properties, such as the oxygen storage capacity of the ceria nanoparticles, requires a fundamental understanding of the $Ce^{4+} \rightarrow Ce^{3+}$ redox cycle.

Several challenges make difficult a fundamental understanding of the processes described above. Feng et al.[4] reported that high-vacuum spectroscopy studies of $CeO_2$ over-estimate the $Ce^{3+}$ concentration due to enhanced surface reduction of ceria in the sample measurement environment. Furthermore, during temperature programmed reaction (TPR) techniques some artifacts can interfere in the interpretation of measurements, e.g. TPR does not take into account the reduction of impurities (nitrates, carbonates).

Neutron diffraction studies by Mamontov et al.[6] on nanoceria identified that the missing intrinsic oxygen ions occupy interstitial sites and are weakly bound in the fluorite lattice, enabling additional defects in the form of anion-Frenkel pairs. However, there remains the need for a capability to examine interstitial oxygen ions' interactions and dynamics in order to understand and improve the catalytic activity of nanoceria and other metal oxides.

Thus, there is a need for a method to obtain quantitative results concerning the $Ce^{3+}$ ions and other metals of lower oxidation state of a redox couple, arising from surface and bulk reduction as well as oxygen vacancy creation and annihilation mechanisms in nanoceria and other metal oxides in order to develop catalytic materials with specific improved properties.

SUMMARY

The present inventors have determined that as opposed to most measurements that have motivated and driven the current understanding of catalysis of metal oxides and most significantly, of $CeO_2$, magnetic measurements can provide quantitative results concerning the ions arising from both surface and bulk reduction. The magnetic susceptibility of the metal oxides may be sensitive to the redox couple if one oxidation state is diamagnetic and the other paramagnetic. Thus, ceria is sensitive to the redox transformation of diamagnetic $Ce^{4+}$ ($4f^0$) to paramagnetic $Ce^{3+}$ ($4f^1$) with $S=1/2$ and $J=5/2$), and the inventors have discovered a method to study the evolution of vacancies and migration of oxygen atoms from inside the ceria structure to its surfaces employing magnetic susceptibility measurement under selected conditions as described herein.

Vincent et al.[7] and Seehra et al.[8] estimated the concentration of $Ce^{3+}$ ions by magnetic susceptibility measurements.

However, the present inventors have discovered that magnetic susceptibility for nanoceria is dependent upon $O_2$ partial pressure and that measurement of the magnetic susceptibility of nanoceria under $O_2$ rich (in air) and deficient (in He) conditions provides a method to determine the intrinsic oxygen storage and release properties of nanoceria, which may be correlated to catalytic activity of that material.

Moreover, the method may be applied to any metal oxide wherein the magnetic susceptibility is sensitive to a redox transformation selected from the group consisting of a diamagnetic oxidation state to a paramagnetic oxidation state, a paramagnetic oxidation state to a ferromagnetic oxidation state and a paramagnetic oxidation state to an antiferromagnetic oxidation state. Such transitions allow the study of the evolution of the metal ions as well as the oxygen vacancies and migration of oxygen atoms from inside the metal oxide structure to its surfaces via magnetic susceptibility measurement according to the embodiments to be described.

Thus, a first embodiment of this application includes a method to predict the catalytic activity of a metal oxide which is subject to one of the listed transformations of formula $M_xO_y$ where x is a number from 1 to 3 and y is a number from 1 to 8. The method includes:

measuring the magnetic susceptibility of a metal oxide sample in an oxygen environment at a specified temperature;

correlating the magnetic susceptibility measured to a value of number of $(M^{d+}$ or $M^{p+}$ or $M^{f+}$ or $M^{a+})$/g ($O_2$ rich)

measuring the magnetic susceptibility of the metal oxide sample in an oxygen free environment at the specified temperature;

correlating the magnetic susceptibility measured to a value of number of $(M^{d+}$ or $M^{p+}$ or $M^{f+}$ or $M^{a+})$/g ($O_2$ deficient)

determining the catalytic active $(M^{d+}$ or $M^{p+}$ or $M^{f+}$ or $M^{a+})$ concentration according to the equation:

$(M^{d+}$ or $M^{p+}$ or $M^{f+}$ or $M^{a+})$/g (active)=[$(M^{d+}$ or $M^{p+}$ or $M^{f+}$ or $M^{a+})$/g ($O_2$ deficient)−$(M^{d+}$ or $M^{p+}$ or $M^{f+}$ or $M^{a+})$/g ($O_2$ rich)]/$(M^{d+}$ or $M^{p+}$ or $M^{f+}$ or $M^{a+})$/g ($O_2$ deficient);

and predicting catalytic activity of the metal oxide sample with the $(M^{d+}$ or $M^{p+}$ or $M^{f+}$ or $M^{a+})$/g (active) value;

wherein the metal of the metal oxide has redox coupled oxidation states wherein the redox transformation is between oxidation states selected from the group consisting of a diamagnetic oxidation state ($M^{d+}$) and a paramagnetic oxidation state ($M^{p+}$), a paramagnetic oxidation state ($M^{p+}$) and a ferromagnetic oxidation state ($M^{f+}$), and a paramagnetic oxidation state ($M^{p+}$) and an antiferromagnetic oxidation state ($M^{a+}$) where d, p, f and a are independently numbers from 1 to 6 and one of the oxidation states ($M^{d+}$), ($M^{p+}$), ($M^{f+}$), and ($M^{a+}$) is formed by reduction by the $O^{2-}$.

In a special aspect of the first embodiment a method to predict the catalytic activity of a nanoceria sample is provided. The method comprises:

measuring the magnetic susceptibility of a nanoceria sample in an oxygen environment at a specified temperature;

correlating the magnetic susceptibility measured to a value of number of $Ce^{3+}$/g ($O_2$ rich) measuring the magnetic susceptibility of the nanoceria in an oxygen free environment at the specified temperature;

correlating the magnetic susceptibility measured to a value of number of $Ce^{3+}$/g ($O_2$ deficient)

determining the catalytic active $Ce^{3+}$ concentration according to the equation:

$Ce^{3+}$/g (active)=[$Ce^{3+}$/g ($O_2$ deficient)−$Ce^{3+}$/g ($O_2$ rich)]/$Ce^{3+}$/g ($O_2$ deficient); and predicting catalytic activity of the nanoceria with the $Ce^{3+}$/g (active) value.

In one aspect of this embodiment, the catalytic activity is for the reduction of NO with CO.

DETAILED DESCRIPTION OF THE PREFERRED EMBODIMENTS

Figure 1:
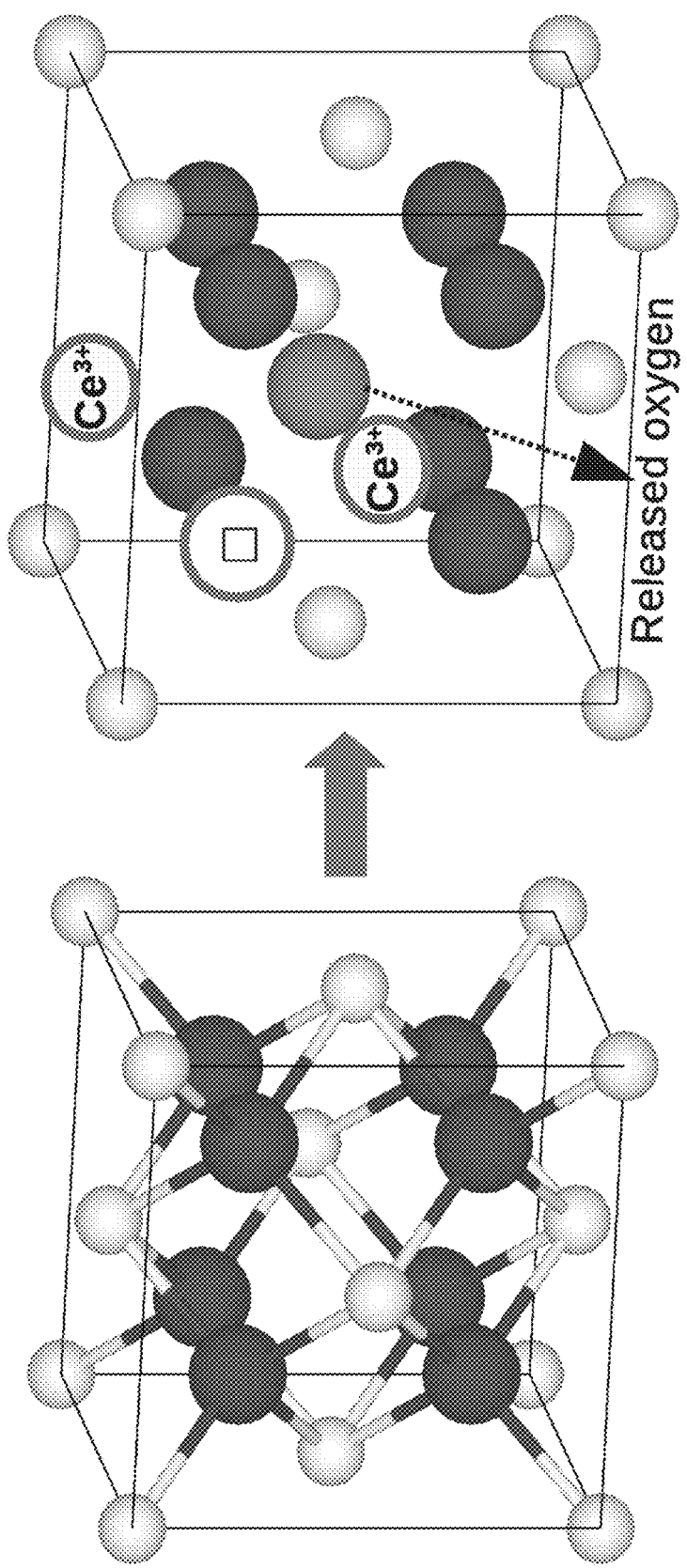
FIG. 1 shows the unit cell fluorite structure of $CeO_2$ before and after vacancy formation.
Figure 2B:
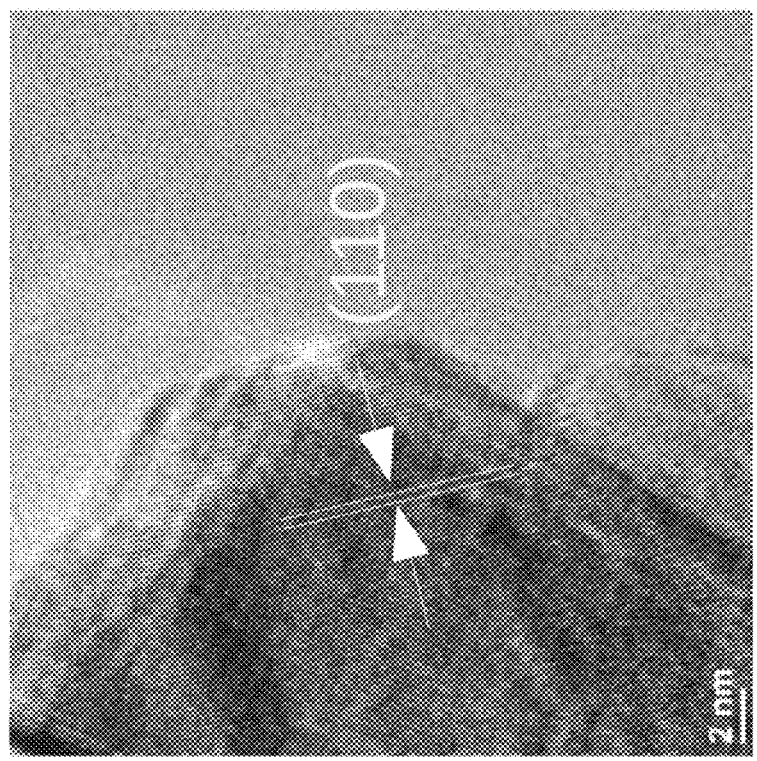
FIG. 2(B) shows a HRTEM image of nanocubes of nanoceria with a 110 plane identified.
Figure 2A:
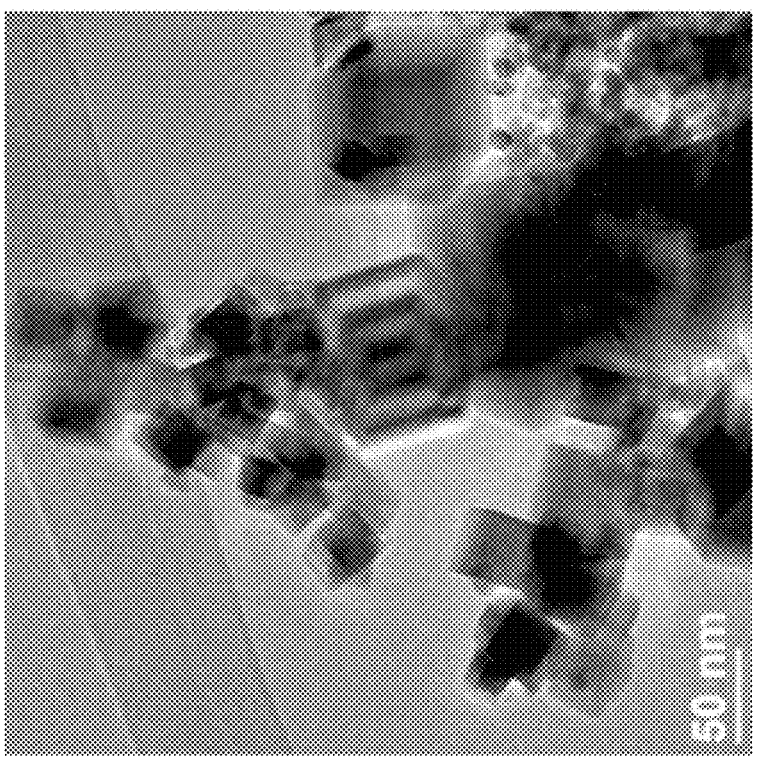
FIG. 2(A) shows a TEM image of nanocubes of nanoceria.
Figure 2D:
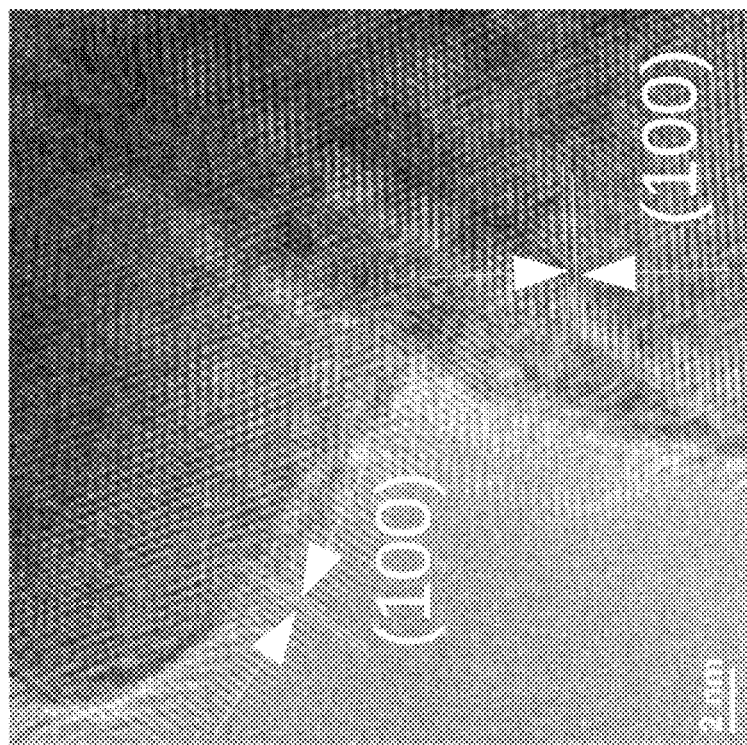
FIG. 2(D) shows a TEM image of nanorods of nanoceria.
Figure 2C:
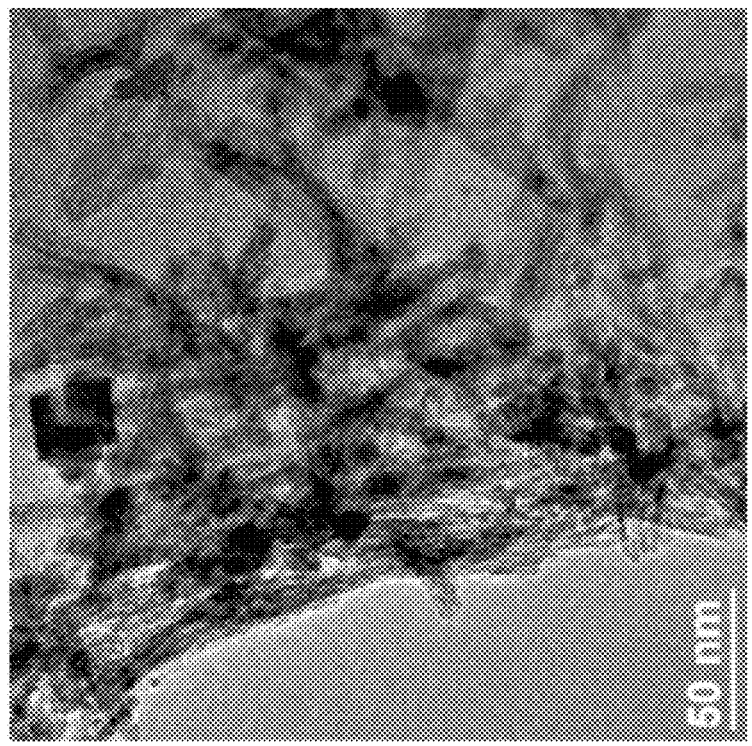
FIG. 2(C) shows a HRTEM image of nanocubes of nanoceria with a 100 plane identified.
Figure 2F:
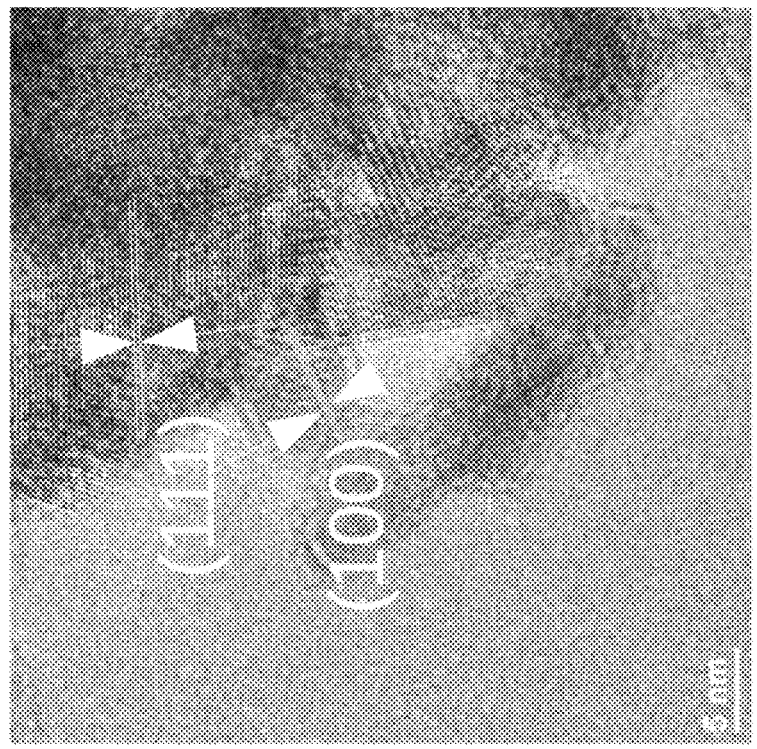
FIG. 2(F) shows a HRTEM image of nanorods of nanoceria with a 100 plane identified.
Figure 2E:
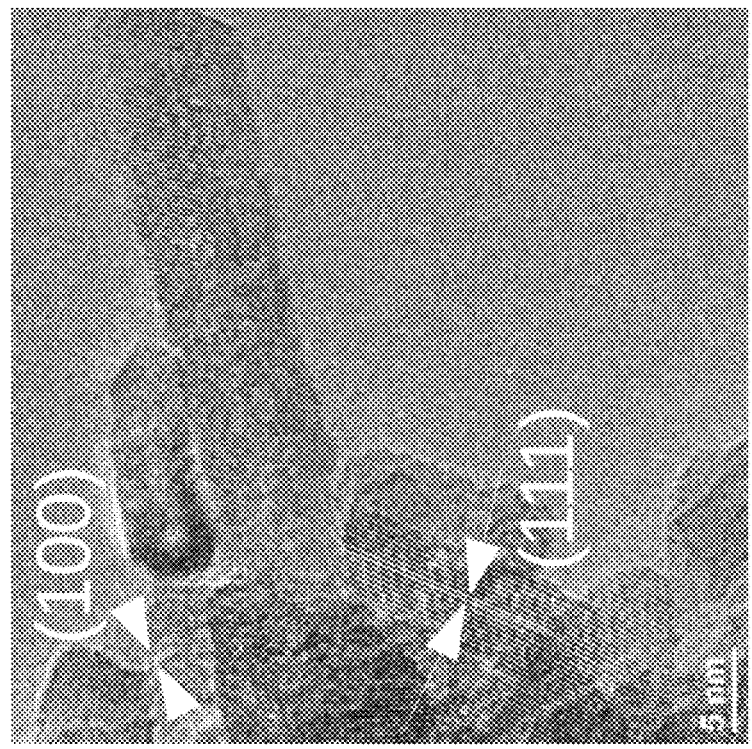
FIG. 2(E) shows a HRTEM image of nanorods of nanoceria with a 111 plane identified.
Figure 2H:
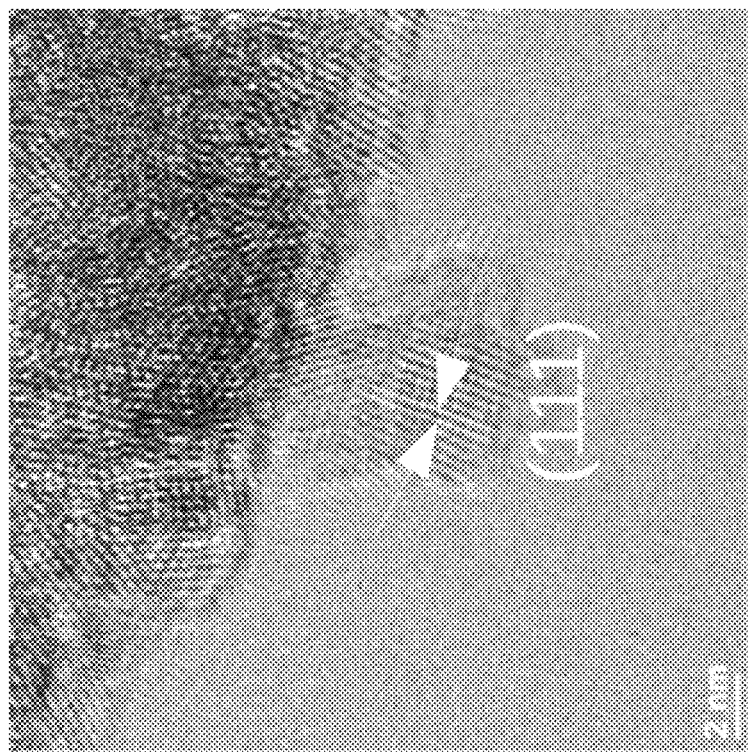
FIG. 2(H) shows a HRTEM image of nanospheres of nanoceria with a 111 plane identified.
Figure 2G:
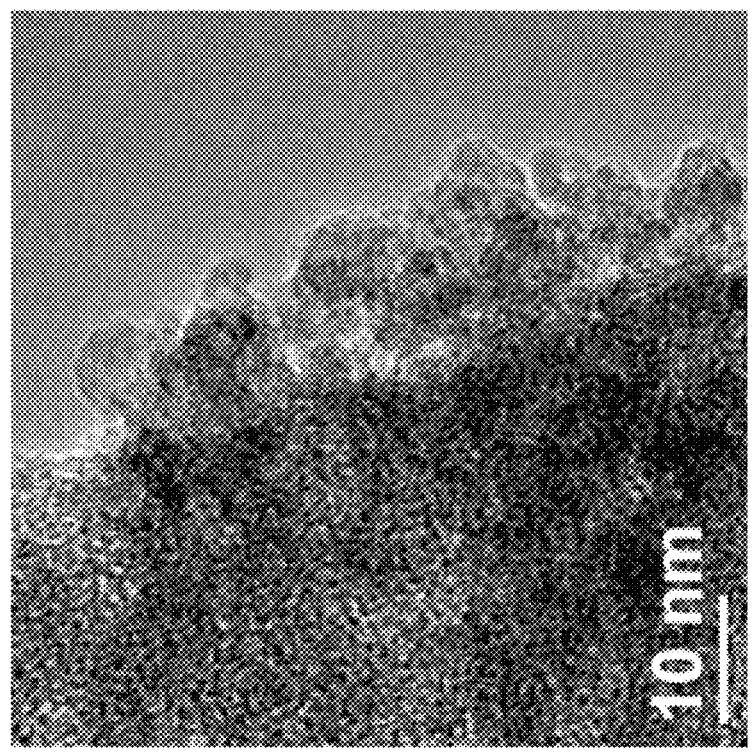
FIG. 2(G) shows a TEM image of nanospheres of nanoceria.
Figure 2I:
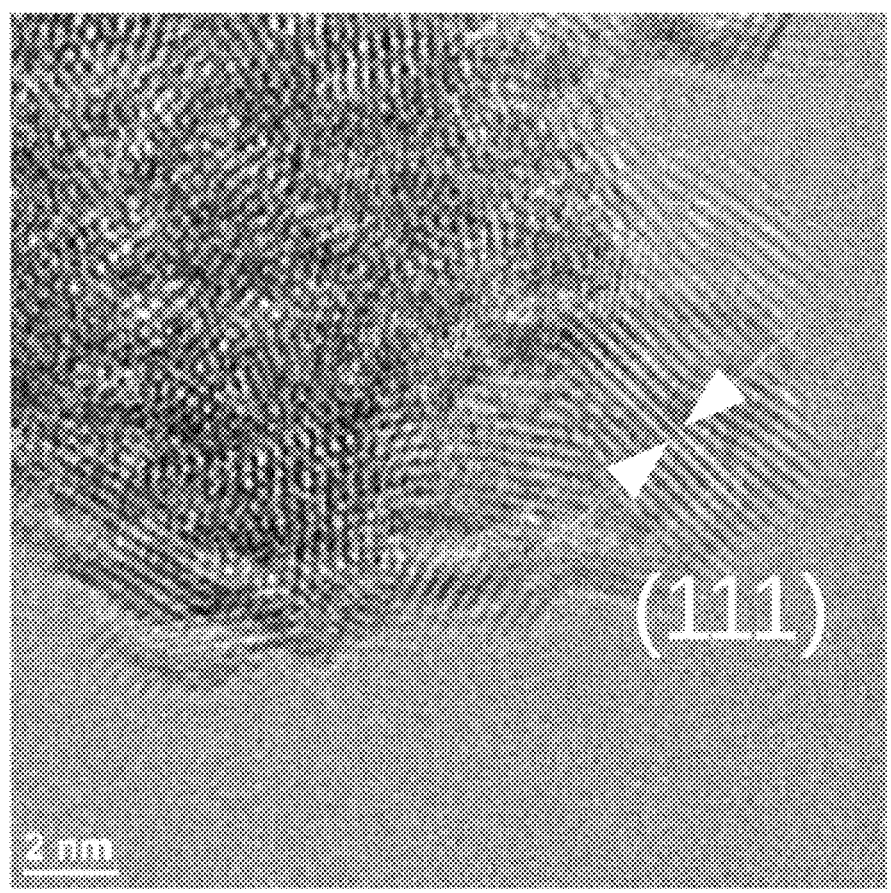
FIG. 2(I) shows a HRTEM image of nanospheres of nanoceria with a 111 plane identified.
Figure 11:
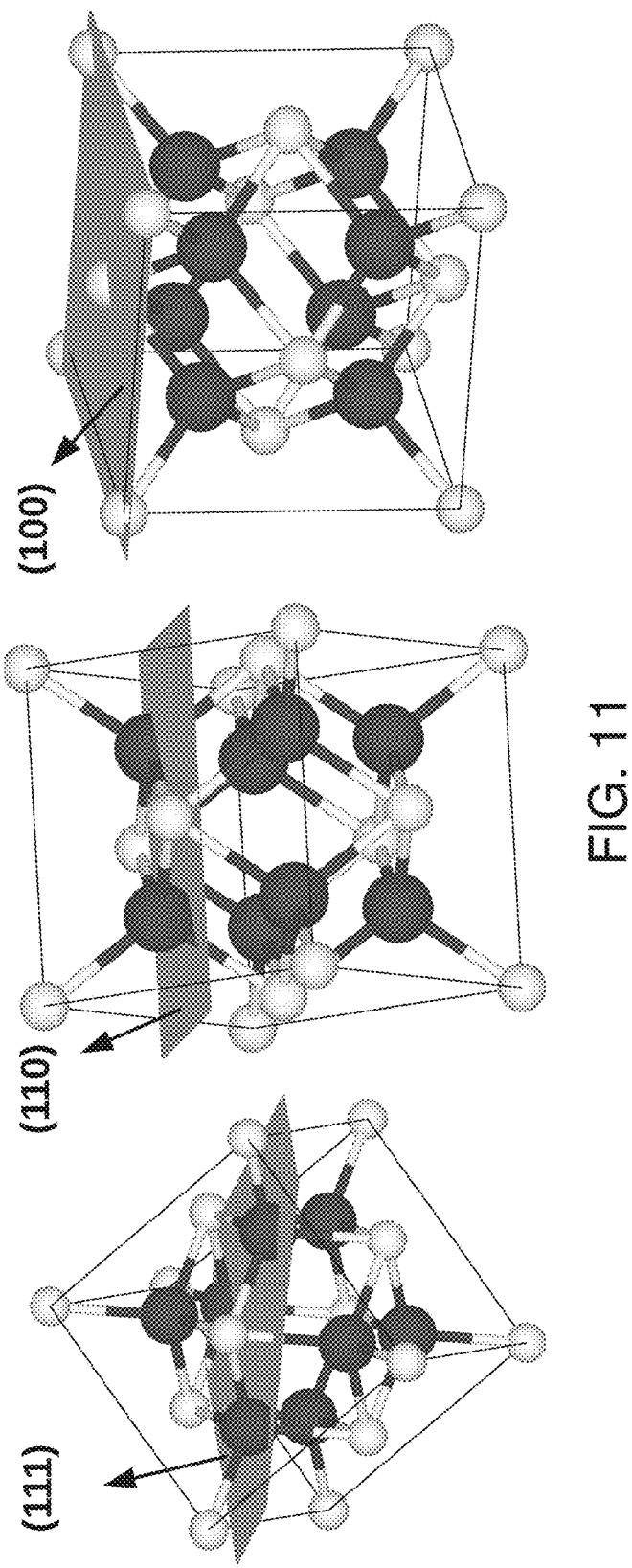
FIG. 11 shows the $CeO_2$ unit cell with the (111), (110), and (100) surface planes identified.

The present inventors have examined the oxygen storage and releasing mechanisms of nanoceria under two different $O_2$ partial pressures ($O_2$ rich-ambient air and deficient-He). The oxygen storage and release properties identified by the magnetic susceptibility are intrinsic to the system; that is, in conventional methods one measures the storage of $O_2$ from gas conversion. In magnetometry, one measures the direct response of the intrinsically present oxygen ions. The main advantages of magnetometry include: (i) the potential to deactivate the active oxygen associated with the high temperatures of gas flow techniques is avoided, (ii) the identified oxygen by magnetometry is due to surface and bulk contributions, and it is dynamic in nature; kinetically transforming $O_{lattice} \leftrightarrow O_{2ads}$ is observed (FIG. 1). Neutron diffraction studies by Mamontov et al.[6] on nanoceria identified that the missing intrinsic oxygen ions occupy interstitial sites, and are weakly bound in the fluorite lattice, enabling additional defects in the form of anion-Frenkel pairs. Currently, there is a lack of clarity on a central issue permitting an understanding of nanoceria's unusual reactivity—quantifying the interstitial oxygen ions' interactions and dynamics. Surface termination configurations control the oxygen vacancy creation, and $Ce^{3+}/Ce^{4+}$ stoichiometry is key to identifying the reduction mechanisms in nanoceria. The modification of the surface termination configurations is permitted by recent developments in the synthesis of shape selected nanoceria of cubes, rods and spheres. While bulk $CeO_2$ exposes preferentially stable (111) planes[9], at the nanoscale, morphology dependent structures can expose less stable (110) and (100) planes (FIG. 11)[10]. Density function theory calculations proposed that surface (100) and (110) planes undergo significant relaxation compared to the (111) planes, and the relative order of surface stability becomes (111)>(110)>(100)[11]. The (111) surface terminations have a Ce:O coordination of 7:3, whereas (110) and (100) surfaces have Ce:O coordinations of 6:3 and 6:2, respectively. Shape selected nanoceria (cubes, rods, and spheres) were synthesized with well-defined crystallographic surface planes (low index planes (111), (110) and (100)) to vary the Ce:O coordination number[12], thereby changing the stability of the planes and concentration of $Ce^{3+}/Ce^{4+}$ and □. FIGS. 2A, 2D, and 2G present the transmission electron microscopy (TEM) images of the nanocubes (25±3 nm), nanorods (length 55±14 nm and width 7±2 nm), and nanospheres (21 nm) respectively. FIGS. 2B and 2C show high resolution transmission electron microscopy (HRTEM) images of the cubes bound by (100) and (110) facets with lattice spacings of 0.27 and 0.19 nm, respectively. FIGS. 2E and 2F show the HRTEM images of rods defined by (100) and (111) facets with lattice spacings of 0.27 and 0.31 nm. FIGS. 2H and 2I show the (111) facet dominated spheres with a lattice spacing of 0.34 nm. The observed HRTEM results are in agreement with previous reports on morphology dependent nanoceria[13-15]: (100) for nanocubes and (111) for nanospheres. It is still an open question as to what planes should be exposed in nanorod ceria. Earlier reports suggest that nanorods expose (100) and (110) planes[13]. However, the inventors' study results indicate clearly that the (100) and (111) surface planes are exposed, which is in agreement with Agarwal et al.'s recent work[16]. Agarwal et al. proposed that the (110) plane is unstable, and the exposure of the (110) or (111) planes is extremely dependent on the synthesis technique.

Figure 3:
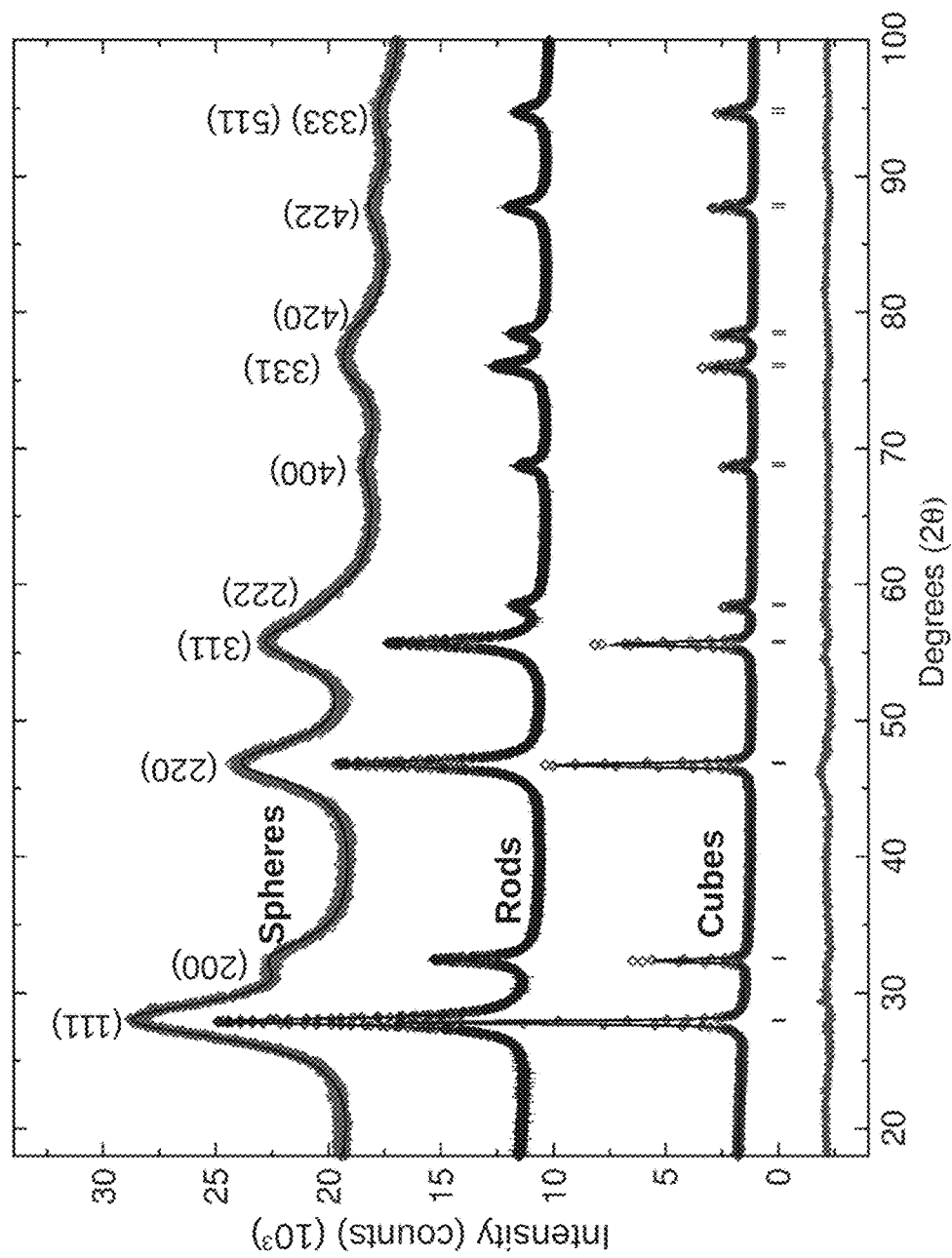
FIG. 3 shows room temperature XRD patterns of $CeO_2$ nanocubes, nanorods and nanospheres.

To further confirm the structure and surface terminations of the different shaped nanoceria, x-ray diffraction (XRD) experiments under ambient conditions were performed followed by full pattern Rietveld refinements using GSAS-II[17] to determine the lattice constants, overall crystallite sizes, and preferred orientations. Room temperature XRD patterns are presented in FIG. 3. In FIG. 3 the (hkl) indices of the structure are labeled. In agreement with previous reports, refinements indicated preferred orientations along the (100) plane for nanocubes, and (111) plane for nanospheres. However, nanorods showed an interesting difference in preferred orientation compared with the HRTEM analysis; no (110) plane preferred orientation. It has been shown by atomic imaging techniques that a reversible dynamic shape evolution of ceria nanoparticles can occur when under electron beam bombardment. The differences between the HRTEM and XRD results of the nanorods is likely due to the (reversible) $Ce^{4+}$ surface reduction resulting in surface reconstruction under electron beam illumination. The inventors' results (refinements) reveal the fraction of nanocubes exposing the (100) and (110) crystal planes are 0.61 and 0.70, and nanorods expose (110) and (100) planes at 0.61 and 0.65 fraction, respectively. Nanospheres provide a smooth distribution of crystallite alignments (powder average) and expose stable (111) planes.

TABLE 1

Crystalline (nanoparticle) diameter (nm) and lattice constant (Å) from XRD pattern refinements, and BET measurements for $CeO_2$ nanocubes, nanorods, and nanospheres.

| shape | size (nm) | α (Å) | BET (m²/g) |
|---|---|---|---|
| nanocubes | 28.0 ± 1.5 | 5.426 ± 0.001 | 35 |
| nanorods | N.A. | 5.427 ± 0.001 | 167 |
| nanospheres | 1.6 ± 0.1 | 5.420 ± 0.001 | 214 |

The Brunauer-Emmett-Teller (BET) method was used with $N_2$ physisorption at its normal boiling point to quantify the specific surface areas of the nanoceria shapes (see Table 1). The specific surface areas (m²/g) calculated with the BET method are consistent with the observed nanoparticle surface-to-volume ratios and their bulk density. From the fraction of exposed planes and the Ce:O coordination of these planes, we calculate 31%, 60%, and 63% of surface $Ce^{3+}$ are present at the exposed surfaces of the cubes, rods, and spheres, respectively.

Nanoceria acts as an oxygen buffer by releasing oxygen through a $Ce^{4+} \leftrightarrow Ce^{3+}$ redox couple. Identifying the structure and exposed crystal planes of $CeO_2$, the present inventors conducted systematic investigations of the effects of oxygen rich and oxygen deficient environments with magnetic susceptibility measurements. Magnetism is a probe of the $Ce^{4+}$ and $Ce^{3+}$ configuration, in addition to the oxygen (through it's antiferromagnetic to paramagnetic transition[32] at around 50 K). The environment sensitive $Ce^{4+} \leftrightarrow Ce^{3+}$ redox property was evaluated by measurement of the temperature dependent magnetic susceptibility of the nanoceria in oxygen rich and oxygen deficient configurations. Nanoceria in the oxygen rich environment was maintained at ambient conditions (approximately 760 Torr), while the nanoceria in the oxygen deficient environment interacts with the 5 Torr helium gas surroundings. Sealing the NMR tubes used to hold the nanoceria during magnetic measurements was done with ECO-BOND (epoxy) under ambient conditions to set the oxygen rich environment. The oxygen deficient sample was allowed to interact with the sample chamber of the magnetic properties measurement system which is at 5 mmHg helium pressure.

In order to investigate the microscopic origin of the redox transformation, temperature dependent magnetic susceptibility measurements were performed. Magnetic susceptibility ($\chi = M/\mu_0 H$ where M is the magnetisation and $\mu_0 H$ the externally applied field) provides a measure of the valence state of the atom or ion. In the simplest case, $\chi$ is described by the following expression.

$$\chi = \frac{Ng_J^2 J(J+1)\mu_B^2}{3k_B T} + \frac{N\mu_B^2}{6(2J+1)}\left[\frac{F(J+1)}{E_{J+1}-E_J} - \frac{F(J)}{E_J - E_{J+1}}\right] = C/T + N\alpha(J)$$

where $F(J)=(1/J)[(S+L+1)^2-J^2][J^2-(S-L)^2]$. C, the Curie constant, gives a direct measure of effective magnetic moment ($\mu_{eff}$) and the number of unpaired (N) electron spins, and the second term $N\alpha(J) \equiv \chi_0$ describes the temperature-independent diamagnetism.

Figure 14A:
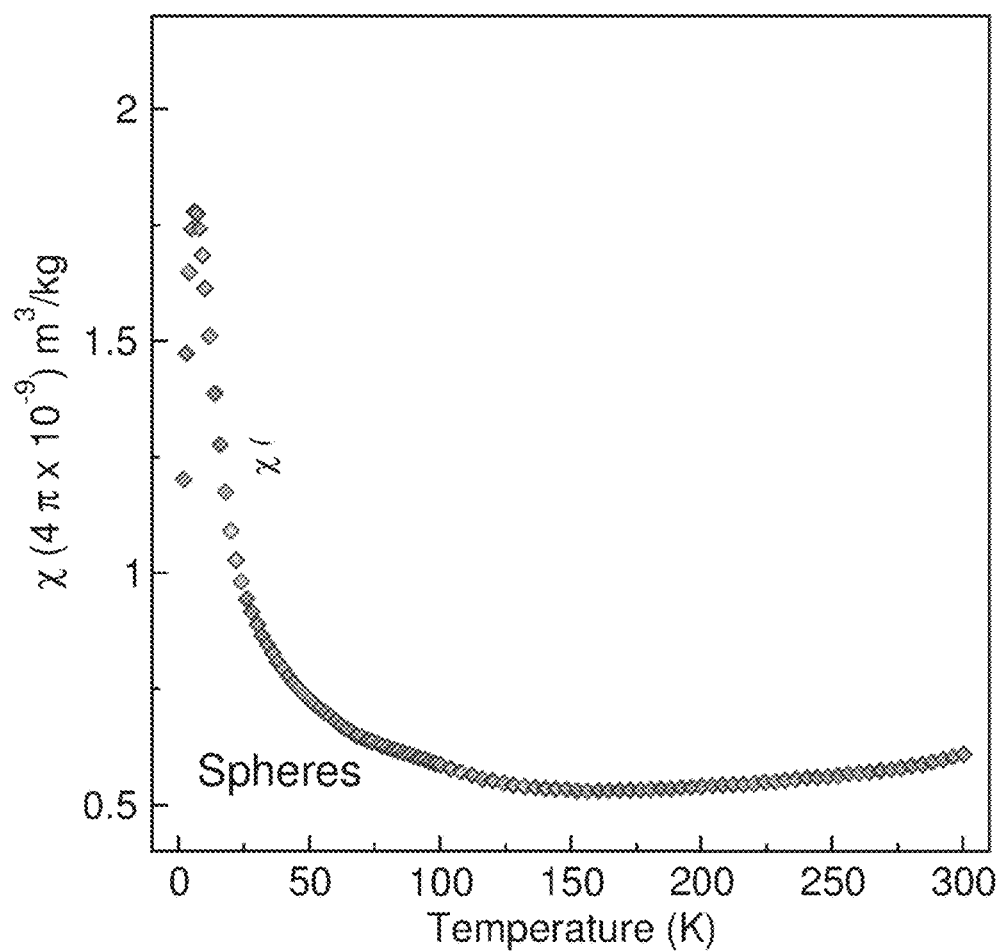
FIG. 14(A) shows magnetic susceptibility $\chi(T)$ of $O_2$ rich nanoceria nanospheres.
Figure 14B:
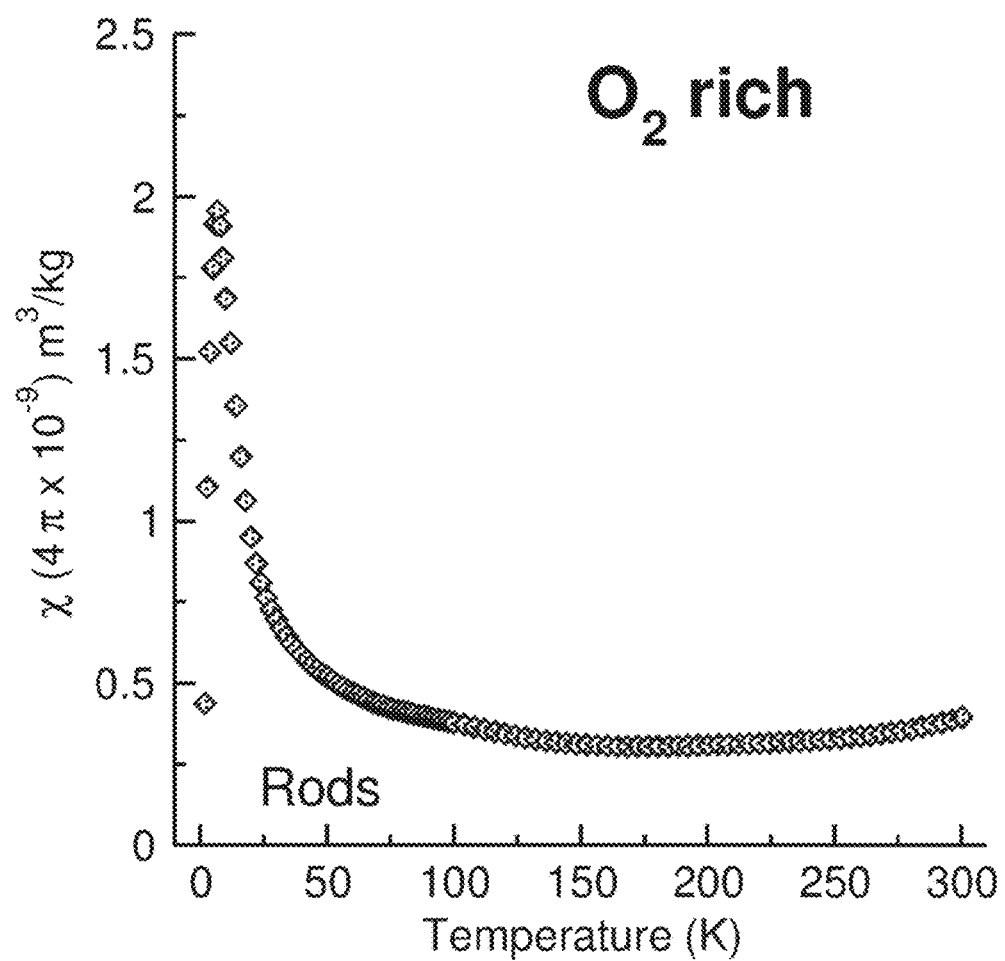
FIG. 14(B) shows magnetic susceptibility $\chi(T)$ of $O_2$ rich nanoceria nanorods.
Figure 14C:
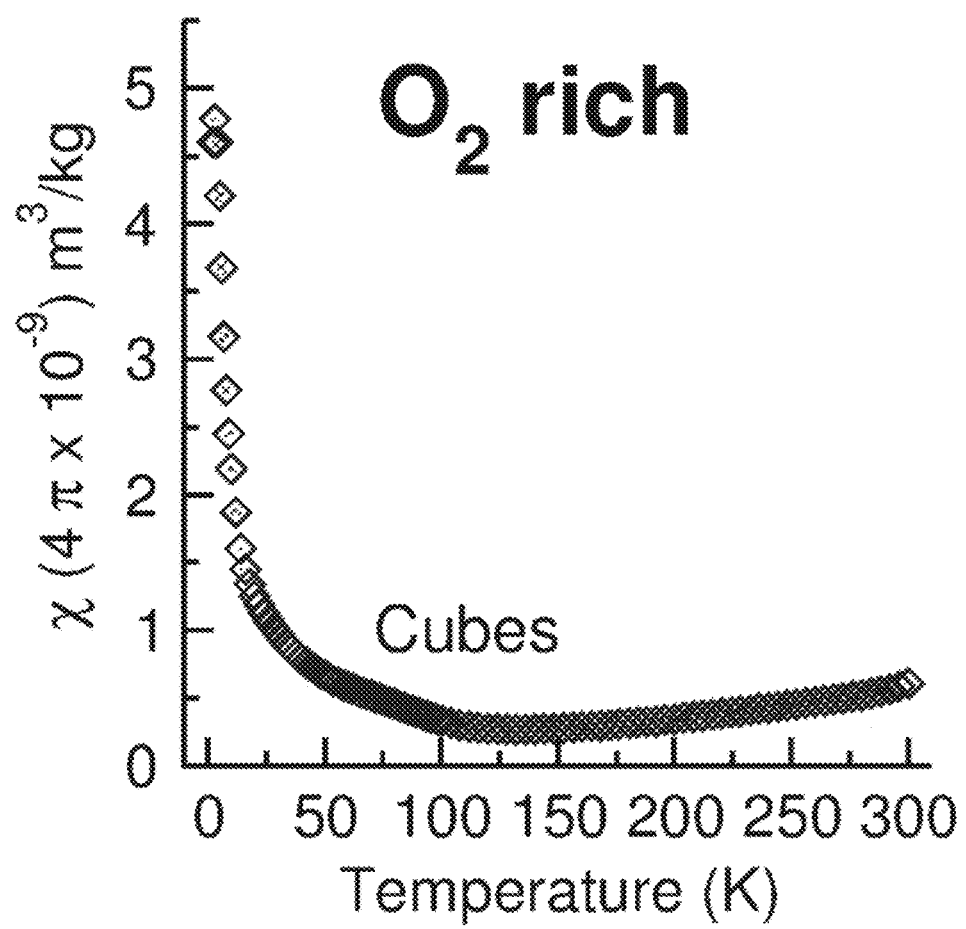
FIG. 14(C) shows magnetic susceptibility $\chi(T)$ of $O_2$ rich nanoceria nanocubes.

$\chi$ vs T of oxygen rich environment samples are shown in FIG. 14. The peak in $\chi(T)$ identifies an antiferromagnetic-to-paramagnetic transition[18]. Fits with $\chi=C/T+N\alpha(J)$ at T>10 K were found, and the corresponding C and $\chi_0$ values for different nanoceria shapes are presented in Table 2.

TABLE 2

Results of Curie law fits to the $O_2$ rich systems' susceptibility. $Ce^{3+}/g$ from $(\chi - \chi_0)^{-1}$ vs T fit with $\chi_0 \equiv N\alpha(J)$, and total number of $Ce^{3+}/g$ for the nanocubes, nanorods, and nanospheres.

| shape | C (4π × 10⁻⁸ m³K/kg) | $\chi_0$ (4π × 10⁻¹⁰ m³/kg) | $Ce^{3+}/g$ (J = ±5/2) |
|---|---|---|---|
| Nanocubes | 2.00 ± 0.03 | 2.52 ± 0.01 | 1.40 ± 0.02 × 10¹⁸ |
| Nanorods | 1.46 ± 0.02 | 2.40 ± 0.02 | 1.02 ± 0.01 × 10¹⁸ |
| Nanospheres | 1.20 ± 0.02 | 4.86 ± 0.04 | 8.39 ± 0.01 × 10¹⁷ |

C quantifies the number of $Ce^{3+}$ in the different shapes and indicates that the increasing $Ce^{3+}$ is in the order spheres to rods to cubes (from $8.0 \times 10^{17}$ $Ce^{3+}/g$ to $1.4 \times 10^{18}$ $Ce^{3+}/g$). However, it was determined that while the $\chi(T)$ may be described, permitting an approximation of the number of $Ce^{3+}$ ions, further improvement of the description may be possible. The energy level diagram of $Ce^{3+}$ (from theory and experiment[19, 20]) is crystal field split from its $^2F_{5/2}$ state into three Krammer doublets with $J_z = \pm 1/2, \pm 5/2$, and $+3/2$. At low temperatures, only the $\pm 1/2$ level is populated, and with increasing temperature, $\pm 5/2$ (at 10 K) and $\pm 3/2$ (at 150 K) levels are also populated[13]. In the cases of J multiplet intervals comparable to kT; that is $E^*_J - E_J$ is approximately kT, it is necessary to use the complete expression of paramagnetic susceptibility. The full formalism for $\chi(T)$ for rare-earth ions in a paramagnetic state, such as $Ce^{3+}$, with the J=1/2, 5/2 and 3/2 states become occupied with warming from below 10 K is $$\chi = \frac{N \sum_J \{[g_J^2 J(J+1)\mu_B^2/3kT] + \alpha(J)\}(2J+1)e^{-E_J^0/kT}}{\sum_J (2J+1)e^{-E_J^0/kT}}.$$

Here $E_J^o$ is the energy of state J in zero field. For the occupation of three J states with 1/2, 5/2, and 3/2, χ(T) becomes $$(\chi - \chi_0) = \frac{N\mu_B^2}{4kT}\left[\frac{g_{1/2}^2 + g_{5/2}^2 e^{-\Delta_1/T} + g_{3/2}^2 e^{-\Delta_2/T}}{1 + e^{-\Delta_1/T} + e^{-\Delta_2/T}}\right]$$

With warming from 10 to approximately 175 K, the J=1/2, 5/2 and 3/2 states become occupied such that:

$$(\chi - \chi_0) = \frac{N\mu_B^2}{4kT}\left[\frac{g_{1/2}^2 + g_{5/2}^2 e^{-\Delta_1/T} + g_{3/2}^2 e^{-\Delta_2/T}}{1 + e^{-\Delta_1/T} + e^{-\Delta_2/T}}\right]$$

where N is the number of $Ce^{3+}$ ions. The energy separation of the states is $\Delta_1$=10 K and $\Delta_2$=150 K, and $g_{1/2}$=2.07, $g_{5/2}$=2.80, and $g_{3/2}$=2.30[13].

Figure 4A:
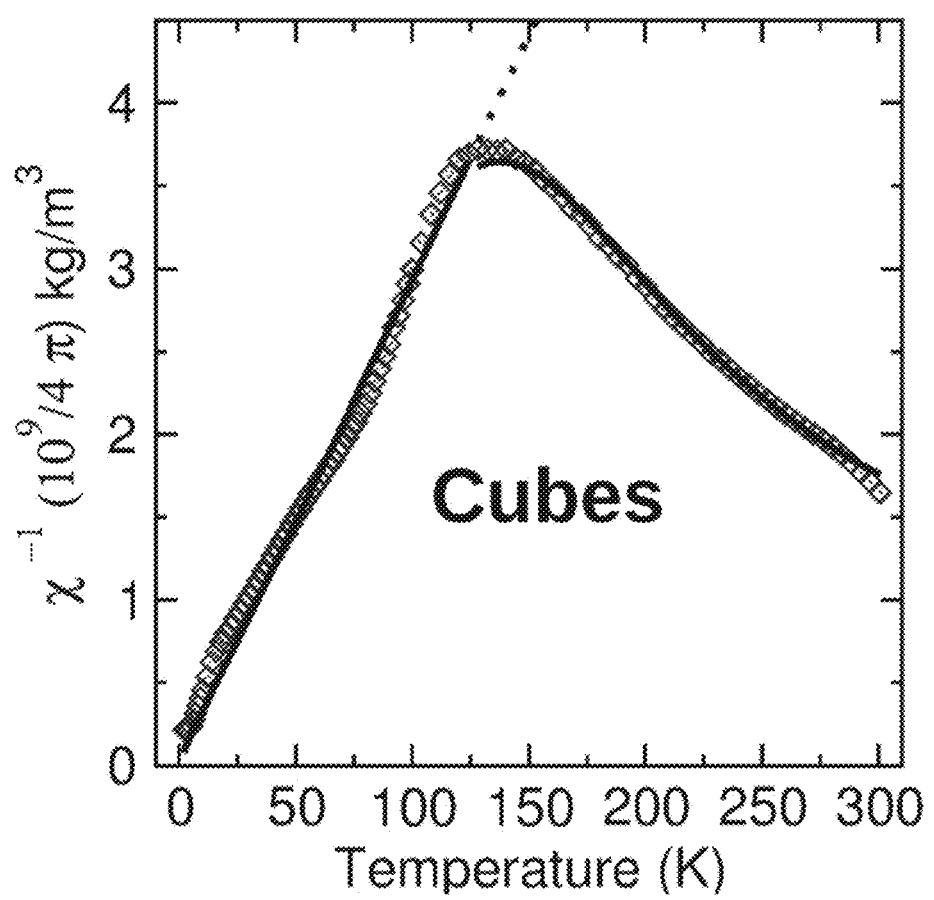
FIG. 4(A) shows inverse magnetic susceptibility $\chi(T)^{-1}$ of $O_2$ rich ceria nanocubes as a function of temperature.
Figure 4B:
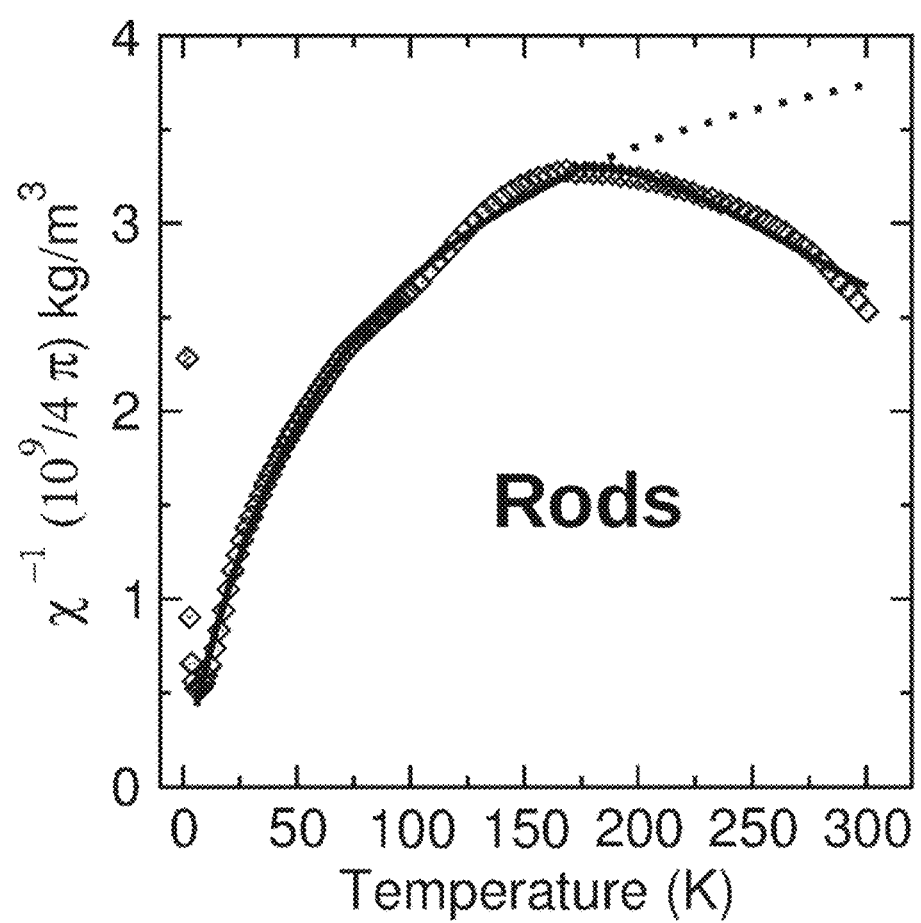
FIG. 4(B) shows inverse magnetic susceptibility $\chi(T)^{-1}$ of $O_2$ rich ceria nanorods as a function of temperature.
Figure 4C:
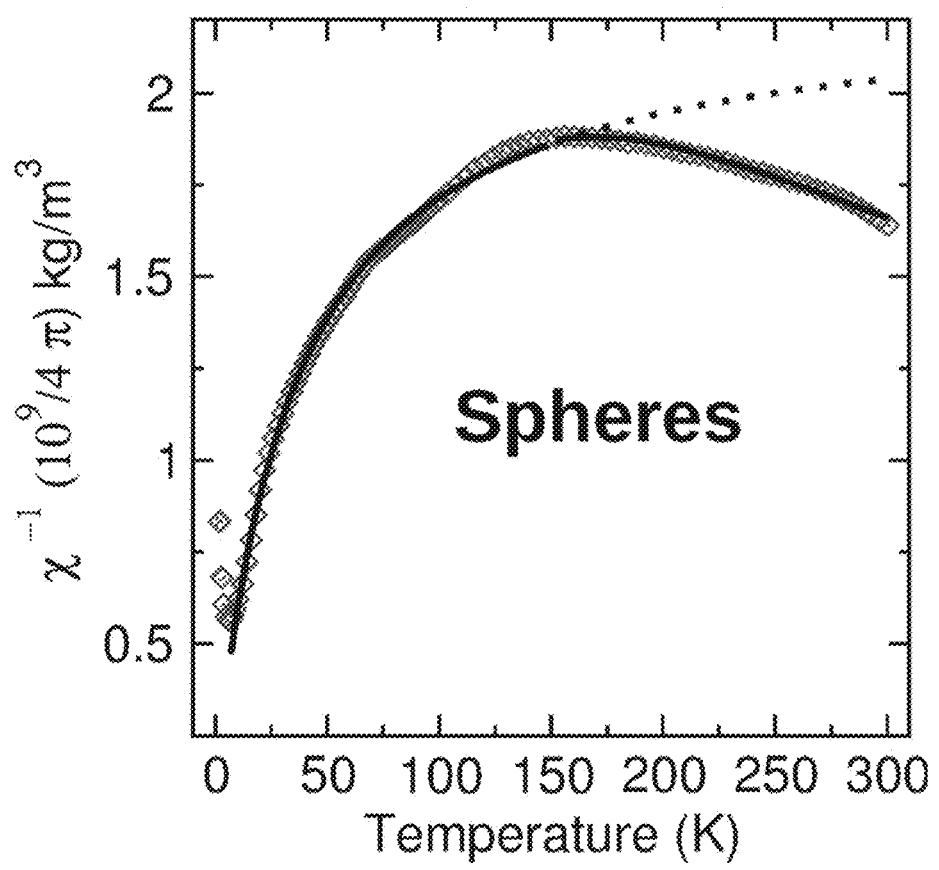
FIG. 4(C) shows inverse magnetic susceptibility $\chi(T)^{-1}$ of $O_2$ rich ceria nanospheres as a function of temperature.
Figure 4D:
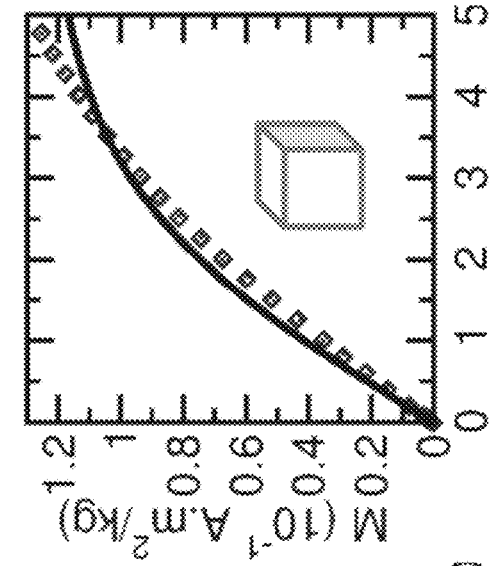
FIG. 4(D) shows the low temperature region of the magnetic susceptibility $\chi(T)$ behavior of all $O_2$ rich nanoceria.
Figure 4E:
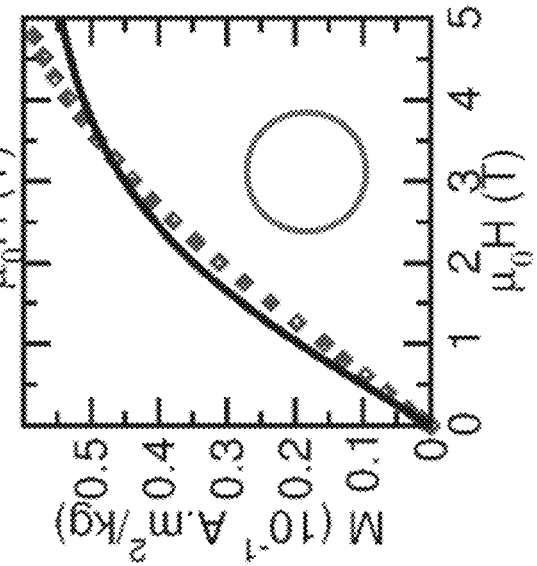
FIG. 4(E) shows the M vs $\mu_0H$ data at 2 K with Brillouin function fits to calculate the number of $Ce^{3+}$/g for nanocubes.
Figure 4F:
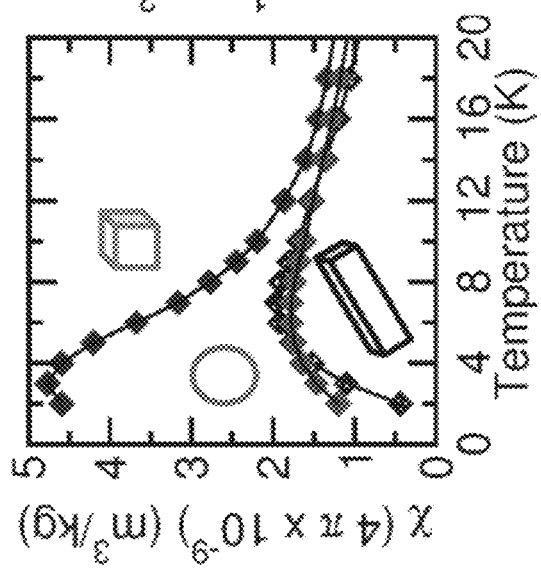
FIG. 4(F) shows the M vs $\mu_0H$ data at 2 K with Brillouin function fits to calculate the number of $Ce^{3+}$/g for nanorods.
Figure 4G:
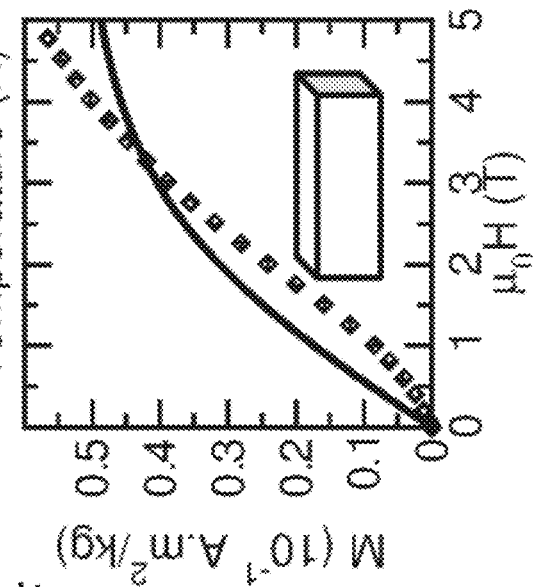
FIG. 4(G) shows the M vs $\mu_0H$ data at 2 K with Brillouin function fits to calculate the number of $Ce^{3+}$/g for nanospheres.

FIGS. 4A, 4B and 4C show the data and fits to the final expression of the susceptibility, $\chi^{-1}$ vs T. The calculated susceptibility expression is shown by the solid lines for the ceria nanocubes, nanorods, and nanospheres. In the high temperature region above $\Delta_2$, an additional term Aexp(−Θ/T) (A is a constant and Θ arises for the thermal excitation of nearby excited levels) is incorporated to describe the effects of thermal expansion of the lattices and its effect on the crystal field splittings. The calculated $Ce^{3+}$ ions/g identified by incorporating crystal field effects are in Table 2 and the $Ce^{3+}$ ions are higher than the simple Curie analysis, where all ions are considered to be in $J_{5/2}$ state. $Ce^{3+}$ ions are increasingly present from spheres to rods to cubes, respectively, going from approximately $1 \times 5 \times 10^{19}$ $Ce^{3+}$/g to approximately $4 \times 10^{19}$ $Ce^{3+}$/g. The origin behind the $Ce^{4+} \leftrightarrow Ce^{3+}$ reduction is due to the removed lattice oxygen (oxygen vacancies) where the excess electrons localize on two cerium atoms turning $Ce^{4+}$ to $Ce^{3+}$. Because the sample is in an oxygen rich environment, the oxygen vacancies responsible for turning the $Ce^{4+}$-to-$Ce^{3+}$ are intrinsic and formed during sample synthesis (the low temperatures of the measurements further suggests that thermal excitations cannot be responsible for this transformation). With more $Ce^{3+}$ and □ intrinsically available, it is expected that the cubes will offer the highest catalytic activity of the shapes. Indeed, to first-order, this is the case (described below).

Interestingly, in the low temperature region (≤10 K) all samples presented a maximum in their susceptibilities. This (T) behaviour may be ascribed to an antiferromagnetic transition, $T_N$ approximately 6 K, of the $Ce^{3+}$ ions. It has been shown in Ce-based compounds that 4f localized $Ce^{3+}$ ions have a tendency to show antiferromagnetism[18, 21, 22], and to further confirm its presence, the field dependent magnetization (M($\mu_0$H)) of nanocubes, nanorods, and nanospheres at 2 K, below $T_N$ and shown in FIGS. 4D-4G, was measured and evidences a meta-magnetic transition. However, in the oxygen rich atmosphere, ceria does not undergo any reduction. To understand the dynamics of the coupled species the susceptibility measurements in an oxygen deficient environment was investigated. The environment selected was a constant 5 Torr helium gas flow sample atmosphere at 2-3 cc/min when the system is at a set-point temperature, and 5-10 cc/min while warming or cooling, depending on the temperature range.

Figure 5A:
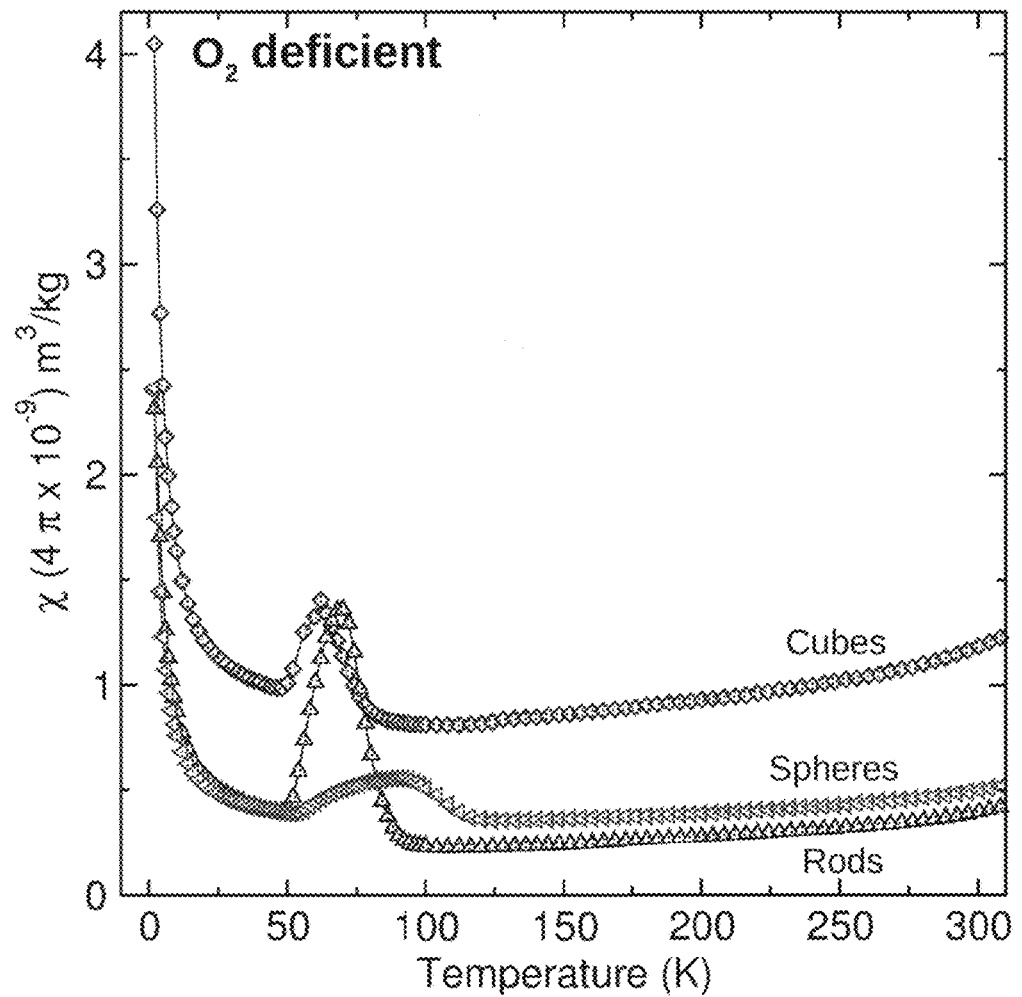
FIG. 5(A) shows magnetic susceptibility $\chi(T)$ of $O_2$ deficient nanoceria shapes.
Figure 5B:
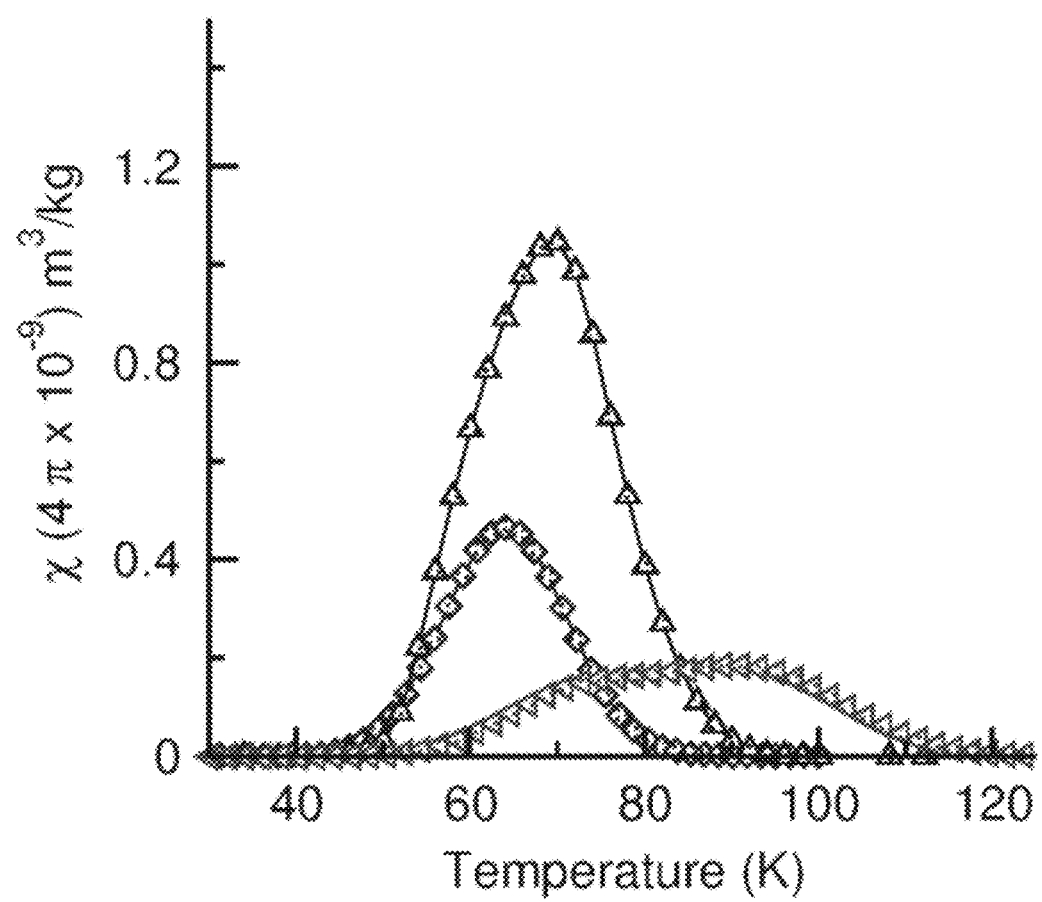
FIG. 5(B) shows the 40-120 K data with background subtraction for each nanoceria shape.

With the intrinsic magnetism of the nanoceria identified, the relationship of the $Ce^{3+} \leftrightarrow Ce^{4+}$ redox transformation and the dynamics of released oxygen in the lattice were studied.

χ(T) measurements of the nanoceria shapes in the $O_2$ deficient environment showed a significantly different magnetic susceptibility compared to the $O_2$-rich environment (FIG. 5A). No antiferromagnetic transition at low temperatures and new broad maxima of χ(T) between 50 and 120 K are observed for all three shapes. FIG. 5B shows the magnitude of the temperature dependent magnetism due to the released oxygen from the system (background subtracted data) of the $O_2$ deficient environment. This comparison of the magnetism of the oxygen rich and oxygen deficient systems showed that the oxygen storage mechanism may be completely different based on the $O_2$ content of the environment. The oxygen dynamics in $O_2$ deficient nanoceria systems is identified by the absence of antiferromagnetic transition. As previously described, in $O_2$ rich systems the $Ce^{3+}$ ions superexchange via $O^{2-}$ ions; that is O is fixed in its crystallographic position. The absence of the low temperature antiferromagnetic transition in the $O_2$ deficient systems indicates that these $O^{2-}$ ions are no longer in their fixed lattice positions and cannot mediate the superexchange interactions of neighboring $Ce^{3+}$ ions; rather, the $O^{2-}$ ions are diffusing through the 'bulk' of the nanoceria to the surface.

Although not wishing to be bound by theory, the inventors believe the occurrence of this broad maximum in χ(T) of the oxygen deficient systems can be understood in the following way. In nanoceria, the carriers responsible for the magnetism are $Ce^{3+}$ and □. At low temperatures, the $4f^1$ localized $Ce^{3+}$ ions act as non-interacting dipoles and their magnetic susceptibility decreases with increasing temperature. However, above approximately 50 K, the susceptibility rises monotonically with warming to a maximum, and decreases with further warming (≤120 K). This response is due to the γ-β antiferro-to-paramagnetic transition of S=1 molecular oxygen ($O_2$)[23]. Magnetic susceptibility studies of adsorbed oxygen on vycor glass, graphite, and zeolites identified this transition and presented similar χ(T) behaviour to that observed in the nanoceria[24-27]. χ(T) from molecular oxygen also broadens depending on the the surface area density and coverage of the oxygen.

The measured χ(T) of nanoceria in a $O_2$ deficient environment clearly indicates that $Ce^{3+} \leftrightarrow Ce^{4+}$ redox reactions result in the supply of reactive oxygen, and this observed intrinsic oxygen is due to the interconversion of $O_{lattice} \leftrightarrow O_{2ads}$, where "ads" denotes the adsorbed oxygen. In nanoceria each Ce atom ([Xe]$4f^1 5d^1 6s^2$) can donate four electrons to the bonding orbitals with two O ($1s^2 2s^2 2p^4$) atoms. When an oxygen vacancy is formed, the two electrons can freely wander in the solid, and these itinerant electrons have a major role in the transformation of $O_{lattice}$ to $O_{2ads}$ in the following way:

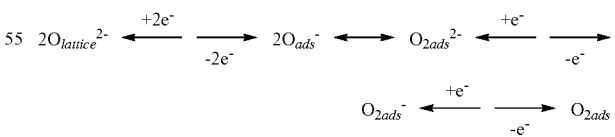

A similar mechanism was described previously for oxidation catalysis of nanoceria[28]

Figure 5C:
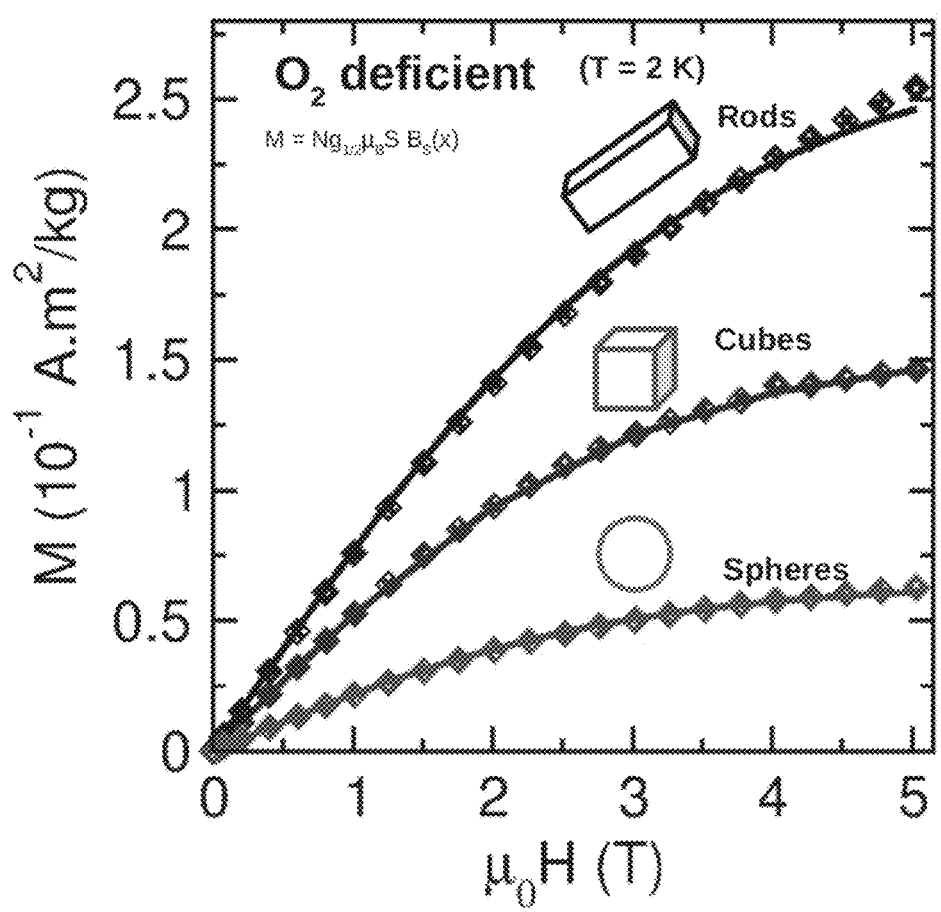
FIG. 5(C) shows M vs $\mu_0H$ data at 2 K of $O_2$ rich nanoceria particles according to shape with Brillouin function fits to calculate the number of $Ce^{3+}$/g.
Figure 15:
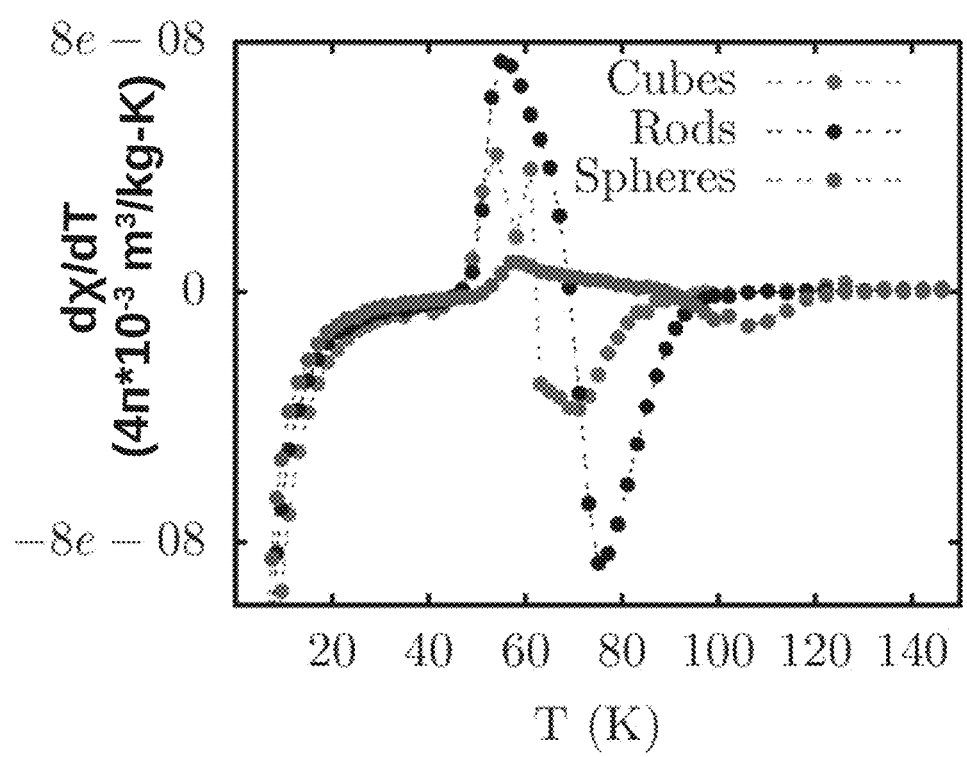
FIG. 15 shows the temperature dependent first derivative of magnetic susceptibility $d\chi/dT$ of the $O_2$ deficient ceria nanoshapes.

The χ(T) measurements are direct evidence that nanoceria releases $O_{lattice}$ due to the gradient in chemical potential with the surroundings. The most plausible explanation for the interaction between released oxygen and nanoceria is adsorption (binding $O_2$ to the lattice). The intrinsic oxygen of ceria which were observed were probably not solely due to the temperature effects, because using the gas flow temperature programmed reaction techniques under ambient conditions identify the lattice oxygen release at approximately 1000 K. Instead, the intrinsic oxygen identified by its magnetism is due to the gradient in concentration with the surroundings. Previously, Mamontov et al.[6] suggested that absorbed oxygen ions in reduced ceria occupy spacious octahedral sites, rather than the vacant tetrahedral sites due to the former being more energetically favourable. The identified intrinsic oxygen is presumably a result of kinetic factors (such as chemical potential gradient) resulting in a dynamic oscillation of $O_{2ads}$ to $O^{2-}_{lattice}$. A more detailed quantitative analysis can be performed in the region of the $O_2$ magnetic transition to obtain the transition temperature and amount of adsorbed oxygen. As a metric to identify the transition temperature, $d\chi(T)/dT$ was determined and a measure of the oxygen magnetic transitions observed for the different shapes obtained; ceria nanospheres have $$T_{N_{O_2}}$$

approximately 80 K, nanorods have $$T_{N_{O_2}}$$

approximately 70 K, and nanocubes have a $$T_{N_{O_2}}$$

approximately 60 K (FIG. 15). The relationship between shape and $$T_{N_{O_2}}$$

indicate the overall amount and strengths of the O—O antiferromagnetic exchange that track with the stored O that percolates from the 'bulk' of the nanoceria onto its surface to become $O_2$ with warming, and the relative impact of the available surface density of the different shapes (e.g. their preferred surface plane areas). This observation is also consistent with the abundance of $O_2$ on the surfaces in relation to the preferentially exposed planes of the different shapes as indicated by the BET analysis. Also, the shape of the maximum and the temperature range over which it spans is related to the nature of the $O_2$ coverage, again tracking with the BET areal densities. The integrated area of $\chi(T)$ over the $O_2$ affected region was ascertained, incorporating the intrinsic (oxygen deficient derived) susceptibility. In the oxygen deficient systems, the $\chi(T)$ response due to the dissipated $O_2$ molecules can be described in a way similar to the Curie constant (C). A comparison has been made to identify and quantify the $O_2$ species in the different shapes. Oxygen has a $^3\Sigma$ ground state with S=1, so the number of $O_{2ads}$/g molecules may be obtained by the expression $$N_{O2ads}/g=(3k\ C)/(\mu_B^2[4S(S+1)+\wedge^2]),$$

where $\wedge$ is the angular momentum quantum of molecular oxygen[29]. The order in which the amount of $O_{2ads}$/g is reacted from the different shapes is rods>cubes>spheres. Quantified intrinsic oxygen storage capacity in μmol $O_2$/g is in the decreasing order of rods (20.1 μmol $O_2$/g) to cubes (8.3 μmol $O_2$/g) to spheres (7.1 mol $O_2$/g). A similar order of the dynamic oxygen storage capacity has been reported by Trovarelli et al.[30] in $Ce_xZr_{(1-x)}O_2$ solid solutions. The stoichiometry indicates that for removal of one lattice oxygen (or formation of $1/2O_2$), two $Ce^{3+}$ and one □ should result. The identified carriers present in the nanoceria cubes, rods, and spheres are given in Table 4. The Mvs $\mu_0$H (2 K) data of oxygen deficient nanoceria was used to ascertain the number of $Ce^{3+}$/g; since the ground state level is populated by $J_z=\pm 1/2$, the data may be fit to the Brillouin function $M=ngS\ \mu_B B_S(x)$, and the fits further confirm that the order of $Ce^{3+}$/g and $O_{2ads}$ is rods>cubes>spheres in the $O_2$ deficient systems (FIG. 5C).

TABLE 4

| | $O_2$ deficient systems: Quantified $O_2$, $Ce^{3+}$ and vacancies (□) of $CeO_2$ | | |
|---|---|---|---|
| Shape | $O_2$/g | $Ce^{3+}$/g | Vacancies (□)/g |
| Nanocubes | 5.00 ± 0.01 × $10^{18}$ | 2.00 ± 0.04 × $10^{19}$ | 1.00 ± 0.02 × $10^{19}$ |
| Nanorods | 12.10 ± 0.10 × $10^{18}$ | 4.85 ± 0.04 × $10^{19}$ | 2.42 ± 0.02 × $10^{19}$ |
| Nanospheres | 4.31 ± 0.01 × $10^{18}$ | 1.73 ± 0.04 × $10^{19}$ | 0.87 ± 0.02 × $10^{19}$ |

Figure 6A:
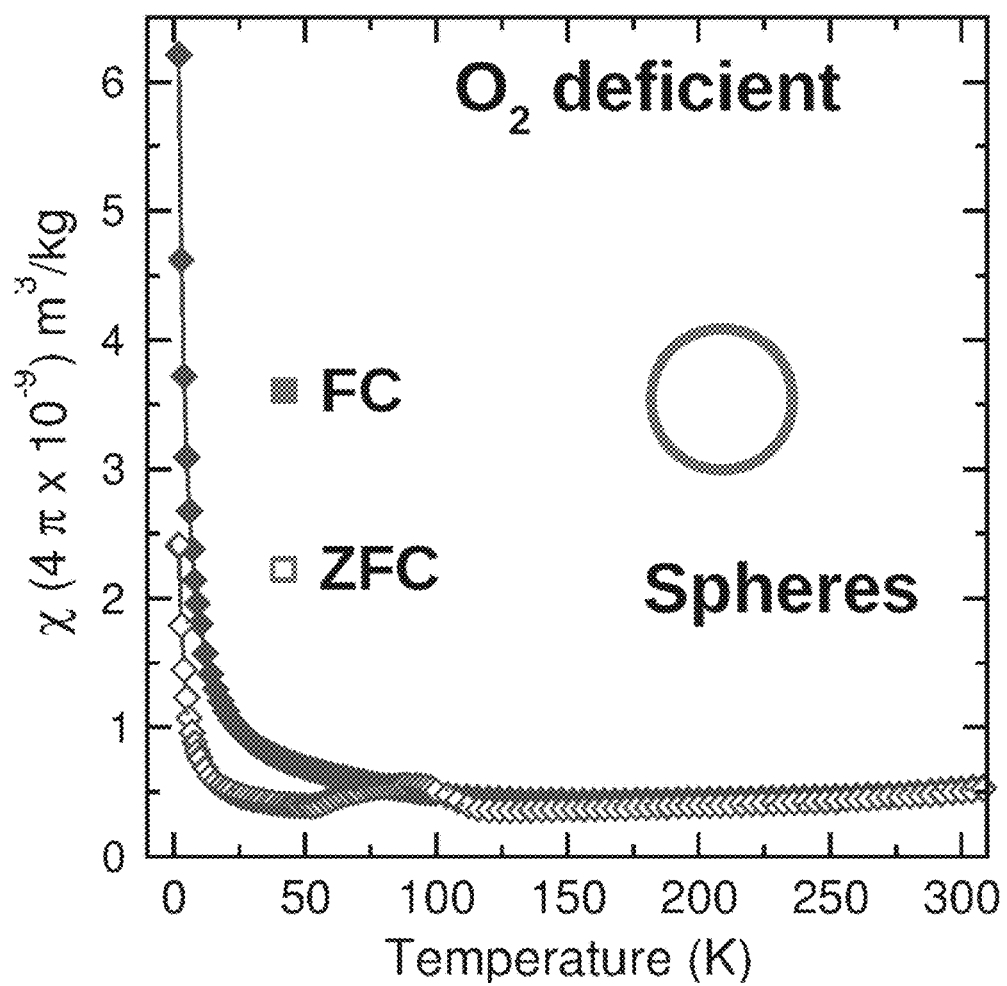
FIG. 6(A) shows the temperature dependence of field cooled ($\chi_{FC}(T)$) and zero field cooled ($\chi_{ZFC}(T)$) magnetic susceptibility for $O_2$ deficient nanospheres.
Figure 6B:
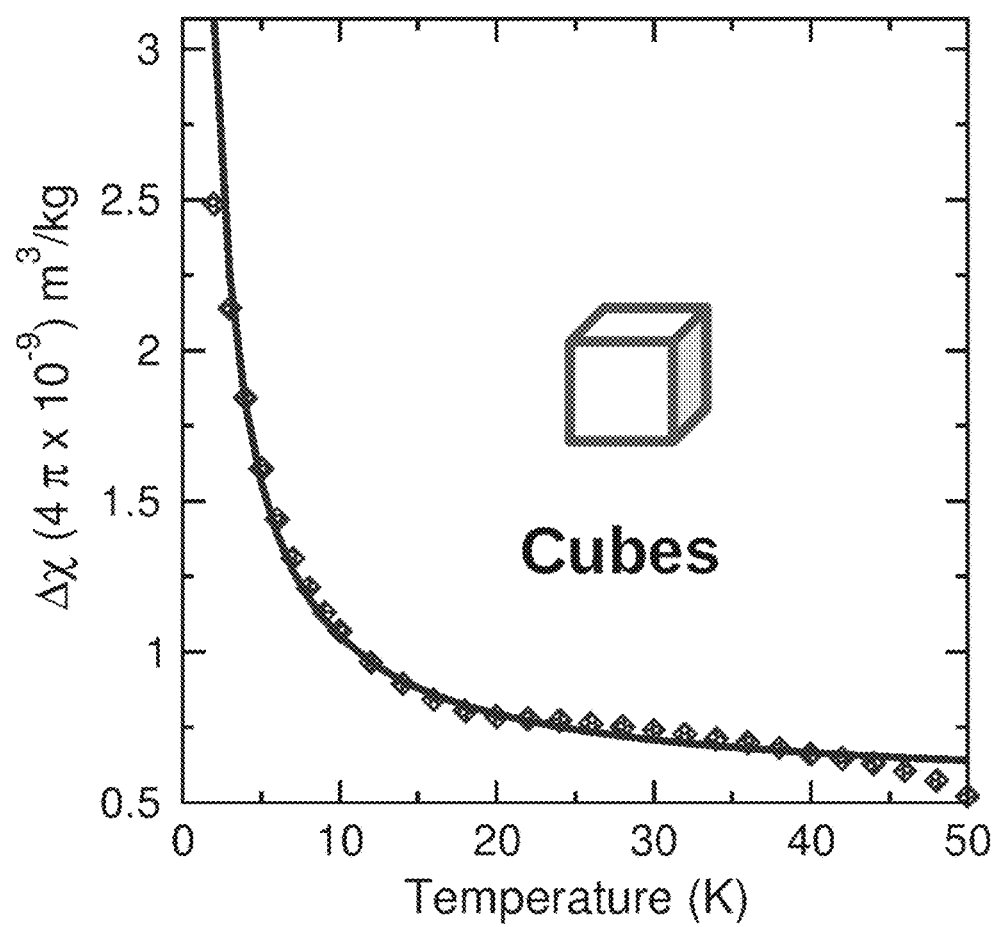
FIG. 6(B) shows the temperature dependence of the difference in the field cooled and zero field cooled magnetic susceptibility $\Delta\chi_{FC-ZFC}$ for $O_2$ deficient ceria nanocubes.
Figure 6C:
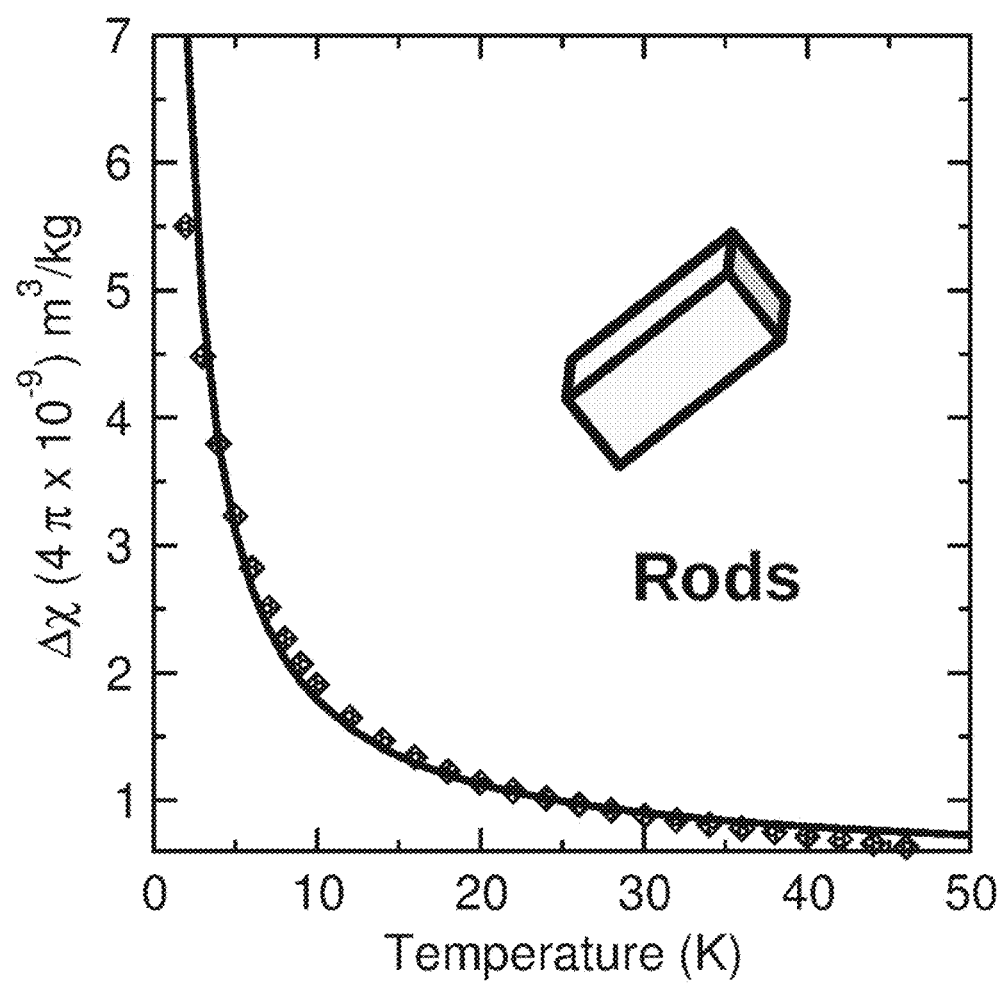
FIG. 6(C) shows the temperature dependence of the difference in the field cooled and zero field cooled magnetic susceptibility $\Delta\chi_{FC-ZFC}$ for $O_2$ deficient ceria nanorods.
Figure 6D:
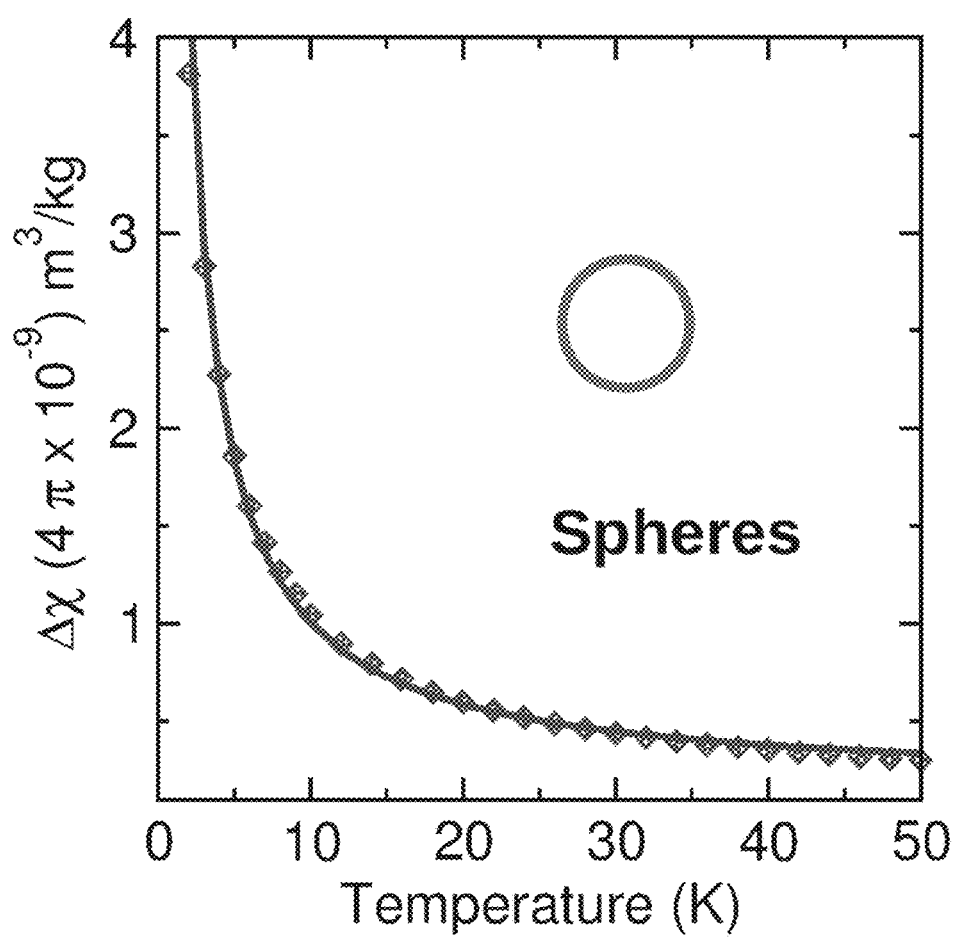
FIG. 6(D) shows the temperature dependence of the difference in the field cooled and zero field cooled magnetic susceptibility $\Delta\chi_{FC-ZFC}$ for $O_2$ deficient ceria nanospheres.
Figure 16A:
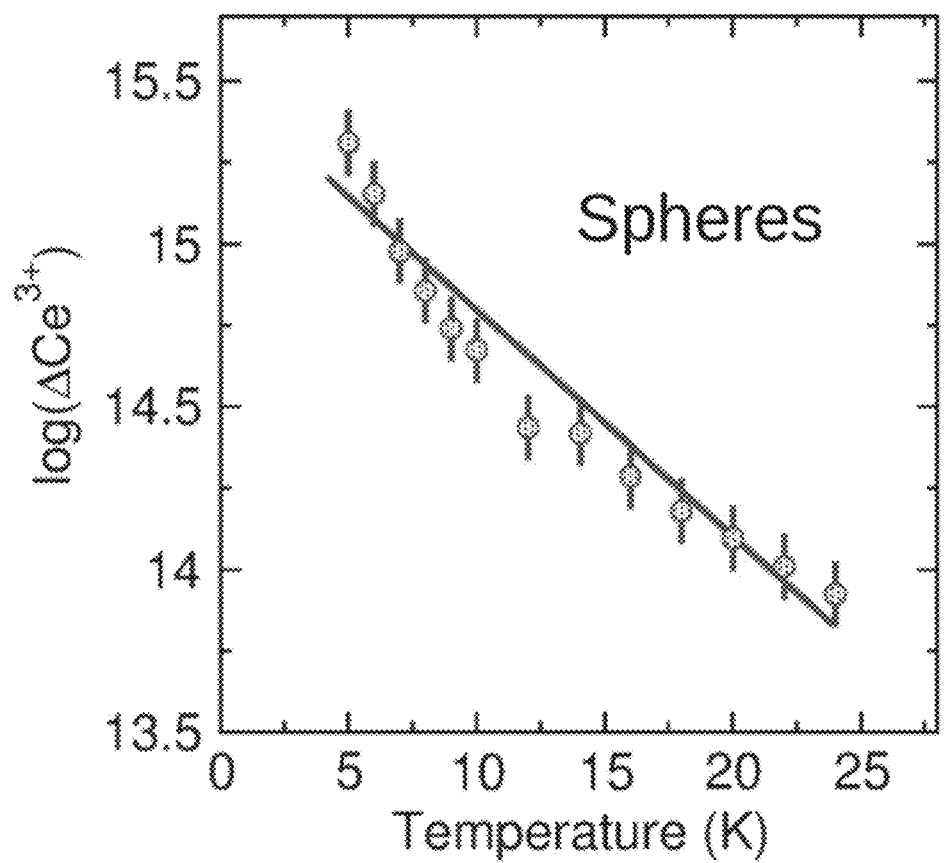
FIG. 16(A) shows the linear fits of logarithm of the difference in $Ce^{3+}$ sites between $O_2$ rich and deficient ceria nanospheres $\log(\Delta Ce^{3+})$ as a function of temperature.
Figure 16B:
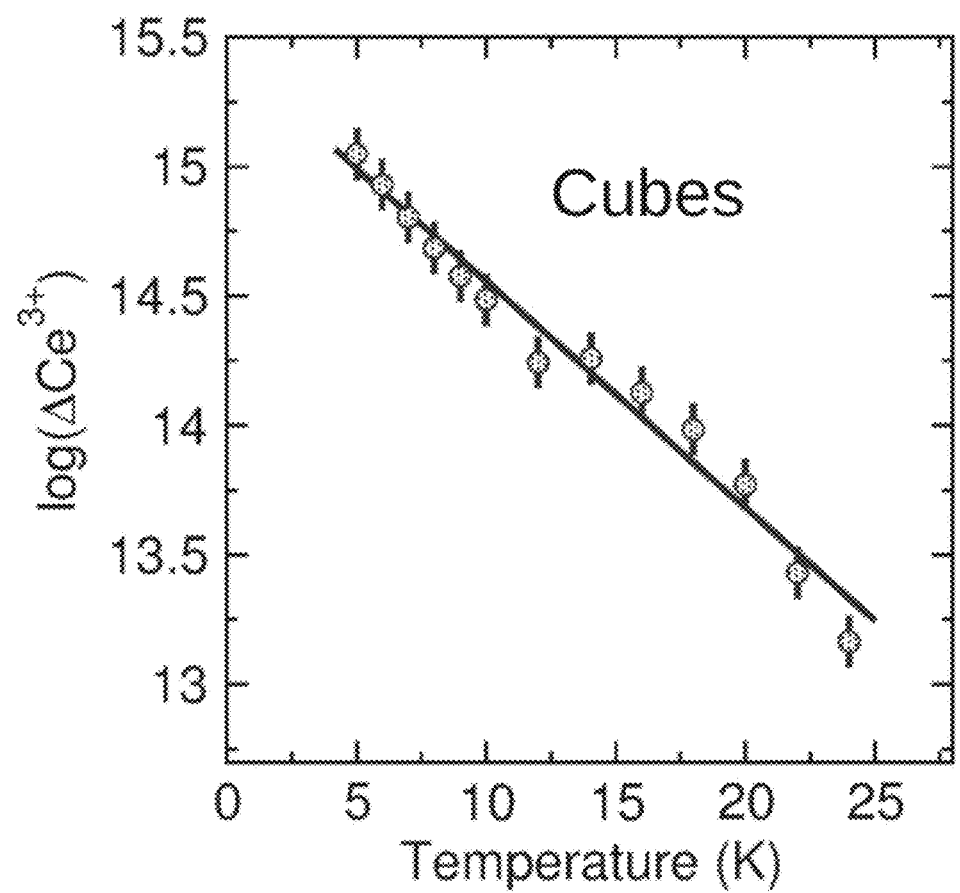
FIG. 16(B) shows the linear fits of logarithm of the difference in $Ce^{3+}$ sites between $O_2$ rich and deficient ceria nanocubes $\log(\Delta Ce^{3+})$ as a function of temperature.
Figure 16C:
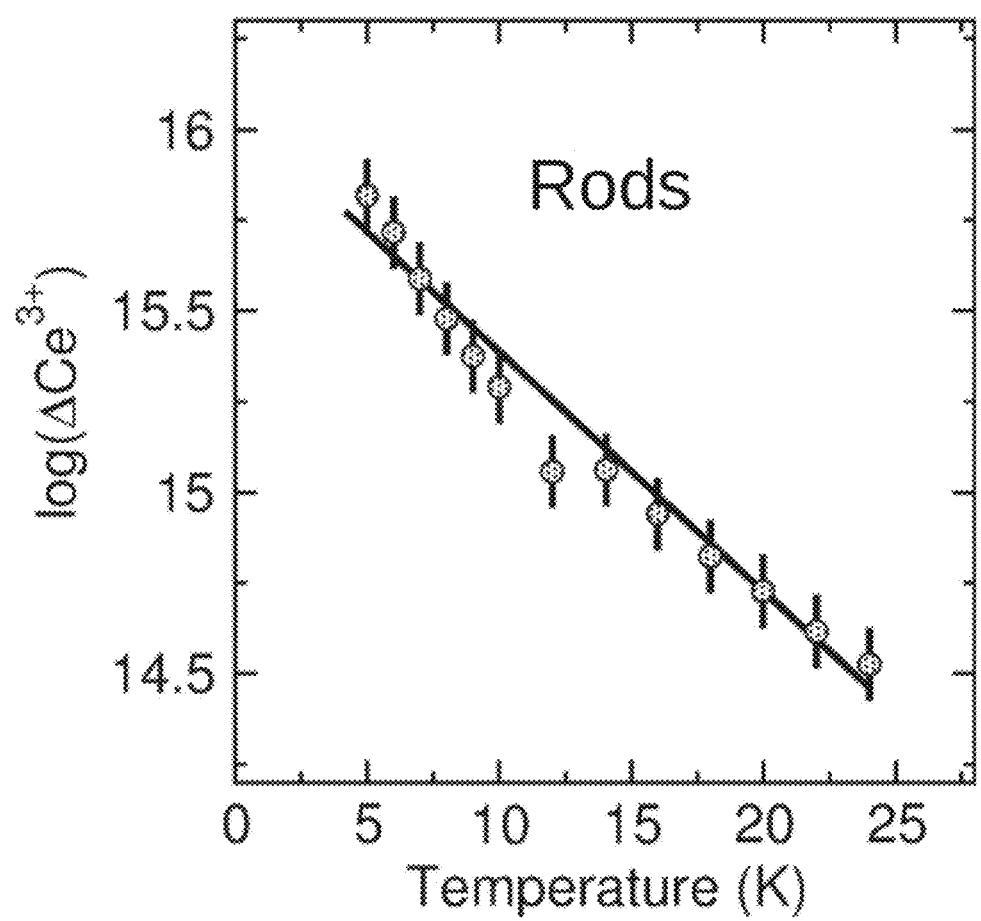
FIG. 16(C) shows the linear fits of logarithm of the difference in $Ce^{3+}$ sites between $O_2$ rich and deficient ceria nanorods $\log(\Delta Ce^{3+})$ as a function of temperature.

Further to the above analysis, the difference between the number of $Ce^{3+}$/g identified by the area under the $\chi(T)$ scan and the 2 KM vs $\mu_0$H data indicates that there is an excess of $Ce^{3+}$ present in the nanoceria. To first order, the origin of this excess $Ce^{3+}$ is from the $O_{lattice}$ to $O_{ads}$ transformation. To quantify the available excess $Ce^{3+}$ ions and get an idea of the kinetics of the $O_{lattice}$ transformation, field-cooled ($\chi_{FC}(T)$) measurements were performed on the $O_2$ deficient nanoshapes. Unlike the $O_2$ rich systems where $\chi_{FC}(T)$ (field cooled) and $\chi_{ZFC}(T)$ (zero field cooled) were identical (not shown), the $O_2$ deficient systems present an irreversibility between $\chi_{FC}(T)$ and $\chi_{ZFC}(T)$ below the respective $O_2$ $T_N$'s, shown in FIGS. 6A-D. The $\chi_{FC}(T)$ measurements identify that $T_N$ is suppressed, and $\chi_{FC}(T)$ is increased significantly for temperatures below where $T_N$ was previously, demarking the increased number of $Ce^{3+}$ ions able to provide a measurable magnetization. The difference between the $\chi_{FX}(T)$ and $\chi_{ZFC}(T)$, $\Delta\chi_{FC-ZFC}(T)$, is shown in FIGS. 6B, 6C and 6D. An increase in number of $Ce^{3+}$/g as a function of temperature that tracks with the number of O that are released as a function of temperature is consistent with an activated energy process (described most simply by an Arrhenius relation) which identifies the energies necessary to migrate O from the lattice of the nanoceria shapes to their surfaces. According to this analysis the nanoceria cubes require ~30% more energy to reduce $Ce^{3+}$ and release O than the nanorods and nanospheres, which involve similar energies. The activation energies from linear fits of $\log_e(\Delta Ce^{3+})$ vs T of the cubes, rods, and spheres are ~8, ~6, and ~6 meV, respectively (FIGS. 16A-C). In addition, the total number of $Ce^{3+}$ ions after incorporating the excess $Ce^{3+}$ ions are presented in Table 5 and map correctly on to the $Ce^{3+}/O_2$ reduction identified by the $\chi_{ZFC}(T)$ maximum between 50 and 110 K. The total number of $Ce^{3+}$/g identified by the sum of M vs $\mu_0$H (2 K) and $\Delta\chi_{FC-ZFC}(T)$ is larger than the number of $Ce^{3+}$/g identified (Table 6) by the $O_{lattice}$-to-$O_{2ads}$ transformations (area under susceptibility) gives an estimation of the role of oxygen vacancies in the $Ce^{3+}$ formation.

That is, if oxygen vacancy creation is the only responsible factor for the $Ce^{3+}$ ion formation the total number of $Ce^{3+}$/g (Table 5) is simply the area under susceptibility. The difference in $Ce^{3+}$ ions is due to the formation of non-oxygen vacancy defects (e.g. Frenkel pairs), and in order of cubes, rods, and spheres are 29%, 19%, and 3% respectively as presented in Table 6.

TABLE 5

$O_2$ deficient systems' data: Number of $Ce^{3+}$ identified by the 2 K M vs $\mu_0$H data and excess $Ce^{3+}$ ions from $\chi_{FC-ZFC}$(T) along with total $Ce^{3+}$ obtained from area under susceptibility.

| shape | $Ce^{3+}$/g (2 K) | $Ce^{3+}$/g ($\chi_{FC-ZFC}$) | $Ce^{3+}$/g |
|---|---|---|---|
| Nanocubes | $1.62 \pm 0.01 \times 10^{19}$ | $1.19 \pm 0.05 \times 10^{19}$ | $2.00 \pm 0.04 \times 10^{19}$ |
| Nanorods | $2.59 \pm 0.03 \times 10^{19}$ | $3.38 \pm 0.05 \times 10^{19}$ | $4.85 \pm 0.04 \times 10^{19}$ |
| Nanospheres | $0.31 \pm 0.01 \times 10^{19}$ | $1.48 \pm 0.02 \times 10^{19}$ | $1.73 \pm 0.04 \times 10^{19}$ |

TABLE 6

$O_2$ deficient systems' data: Total number of $Ce^{3+}$ identified by the sum of 2 K M vs $\mu_0$H data and excess $Ce^{3+}$ ions from $\chi_{FC-ZFC}$(T) along with total $Ce^{3+}$ obtained from area under susceptibility.

| shape | M vs $\mu_0$H (2 K) + $\chi_{FC-ZFC}$ (T) | $Ce^{3+}$/g | % difference |
|---|---|---|---|
| Nanocubes | $2.81 \pm 0.05 \times 10^{19}$ | $2.00 \pm 0.04 \times 10^{19}$ | 29 |
| Nanorods | $5.97 \pm 0.06 \times 10^{19}$ | $4.85 \pm 0.04 \times 10^{19}$ | 19 |
| Nanospheres | $1.79 \pm 0.02 \times 10^{19}$ | $1.73 \pm 0.04 \times 10^{19}$ | 3 |

Figure 7A:
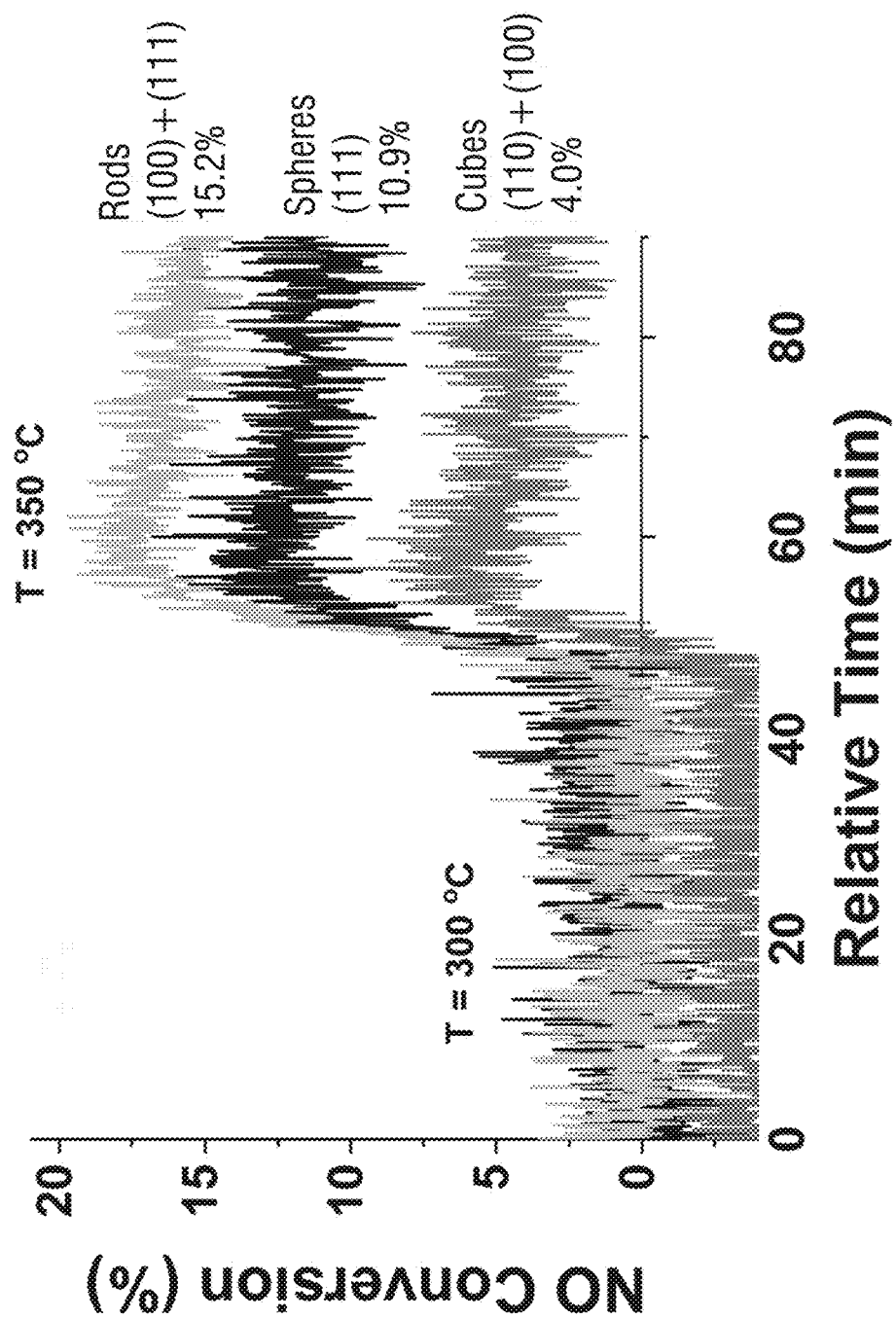
FIG. 7(A) shows NO conversion as a function of time during steady state NO reduction by CO at 300° C. and 350° C. for nanoceria shapes.

The relationship between the structure and magnetism and catalytic activity of the various nanoceria shapes was examined by performing the steady-state reaction of NO reduction by CO. Differential conversions were achieved at 350° C. for a reactor with a constant loading of 50 mg of nanoceria catalyst. The above magnetic analysis revealed that the surface reduction of $Ce^{4+}$-to-$Ce^{3+}$ is favored in the order of cubes (110)+(100), rods (110)+(111), and spheres (111), with crystal planes determined by XRD and HRTEM. The catalytic performance, therefore, is expected to follow the same trend. FIG. 7A shows that the conversion varies as rods (110)+(111)>spheres (111)>cubes (110)+(100). Based on the conversions alone, the trend in catalytic performance does not agree with expected performance. The discrepancy may be attributed to differences in $Ce^{3+}$ concentration-per-mass and specific surface area (SSA) between the various $CeO_2$ nanoshapes. Because the same mass of catalyst was used (50 mg), normalization of activity or $Ce^{3+}$ on a per-mass-of-catalyst basis does not yield any correlation with the trends in $Ce^{3+}$/g (see Examples). Catalysis is a surface phenomenon, thus the appropriate parameters should be normalized in a way that captures the interaction of the NO and/or CO reactants with the catalytic surface sites on the various nanoceria. Therefore, it is most appropriate to use the SSA to normalize the rate and determine the $Ce^{3+}$ surface density ($Ce^{3+}$/nm$^2$).

Figure 17A:
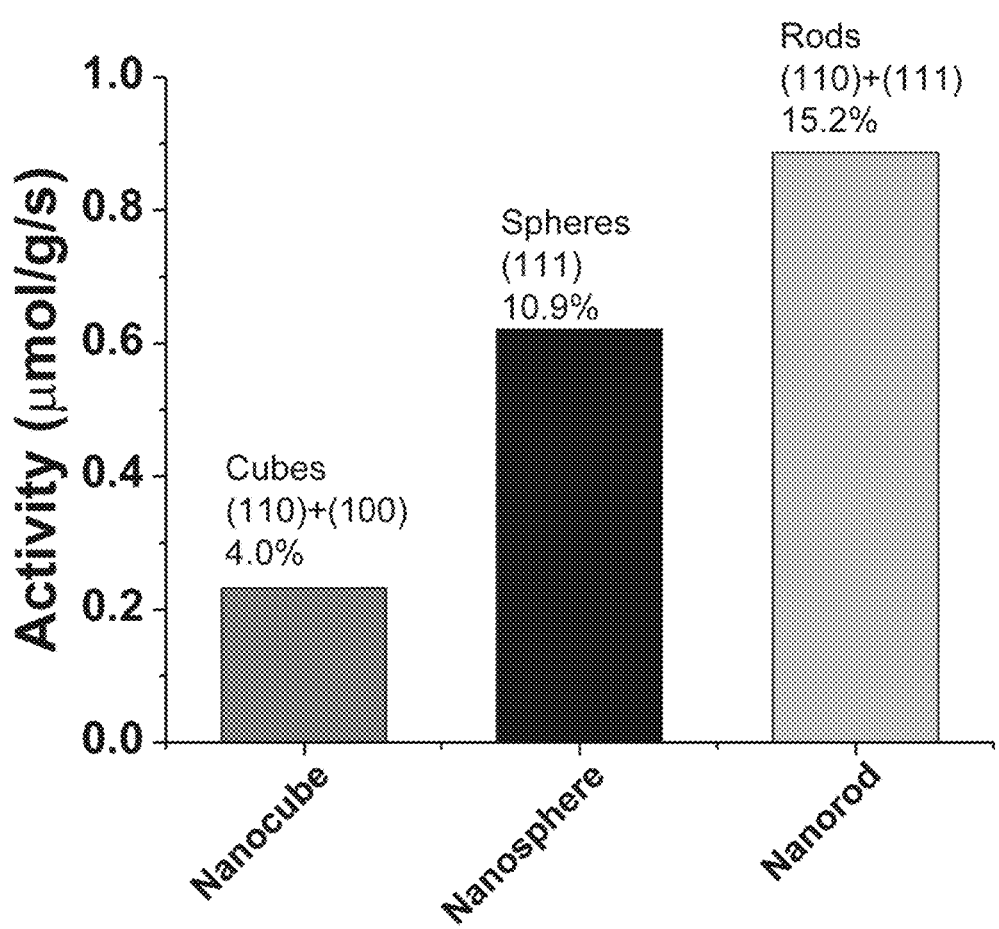
FIG. 17(A) shows the catalyst mass normalized NO reduction activity at 350° C. for the ceria nanoshapes.
Figure 17B:
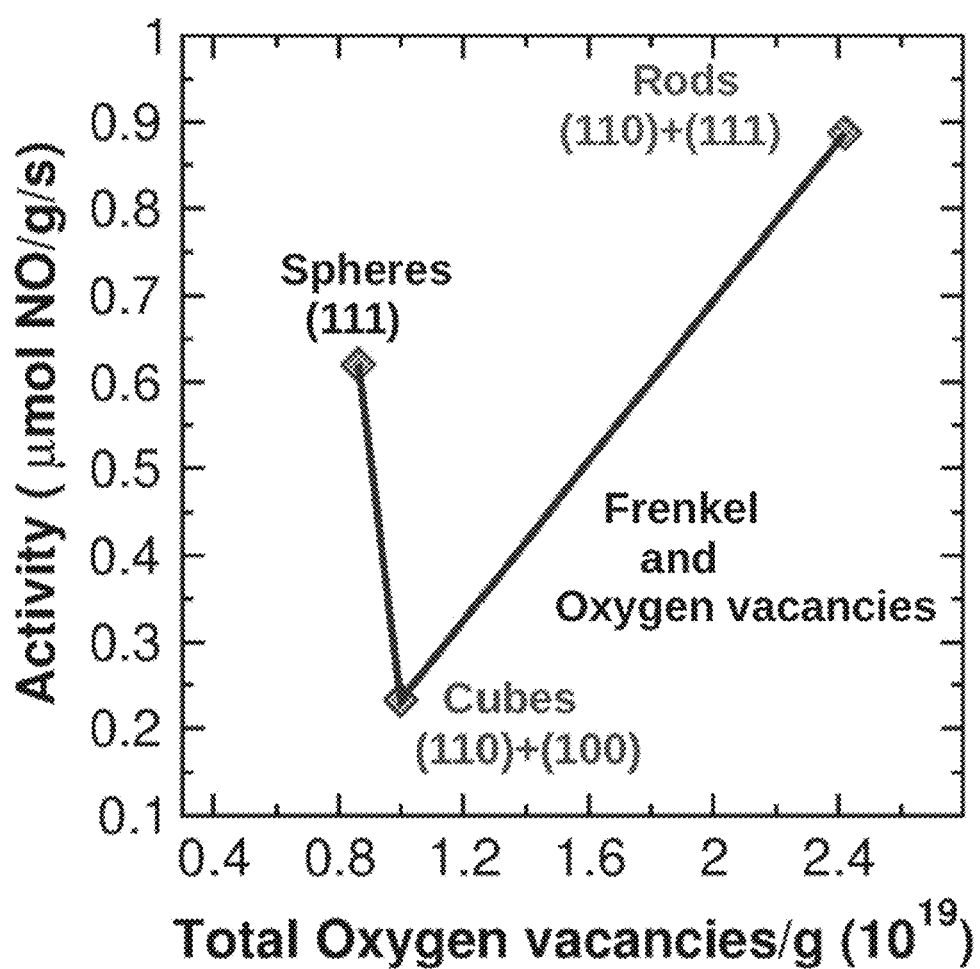
FIG. 17(B) shows the catalyst mass normalized NO reduction activity at 350° C. as a function of the total oxygen vacancies (vacancies and Frenkel defects) for the ceria nanoshapes.
Figure 17C:
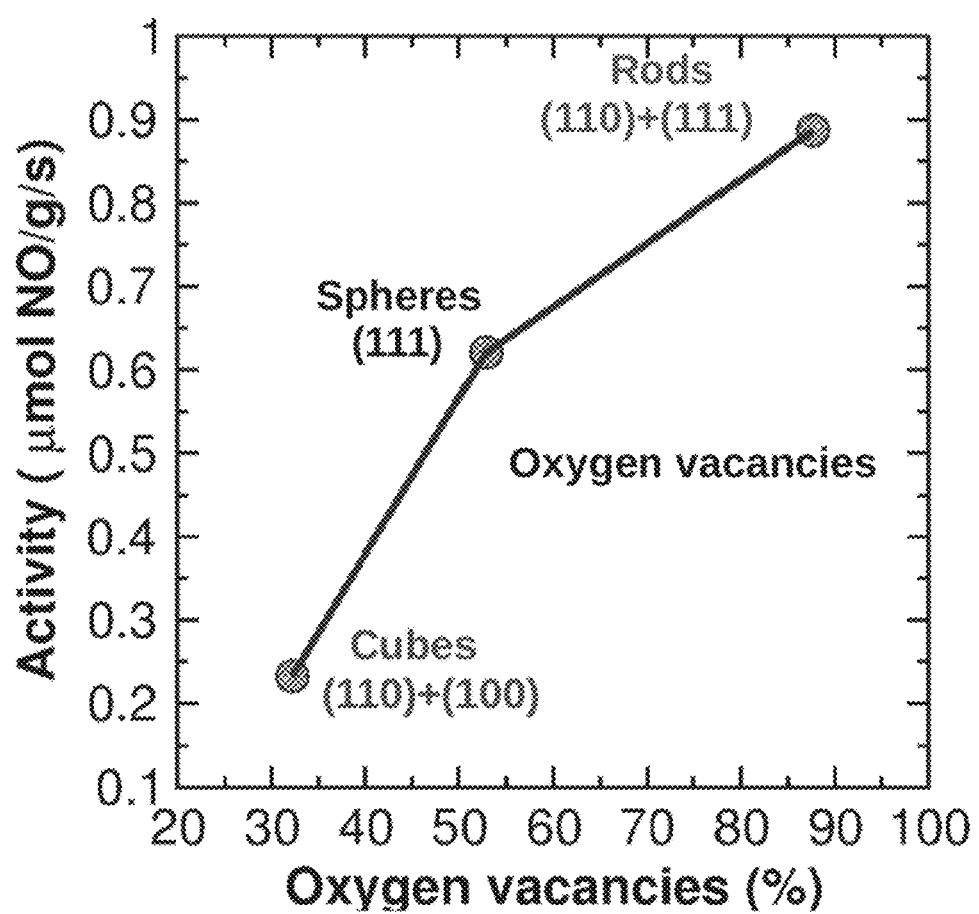
FIG. 17(C) shows the catalyst mass normalized NO reduction activity at 350° C. as a function of the oxygen vacancies only (no Frenkel defects) for the ceria nanoshapes.

Ceria is an important catalytic material, especially for automotive emissions control. Therefore, the relationship between the structure, $Ce^{3+}$, and catalytic activity of the various nanoceria shapes was examined by performing steady-state reduction of NO by CO at 350° C. with the different nanoceria. As shown in FIG. 7A), the conversion was negligible below this reaction temperature, but reached a stable steady state within 1 h of achieving the reaction temperature. Conversions at 350° C. were deliberately maintained below ~15% by using a constant 50 mg of each catalyst, such that accurate reaction rates could be calculated without reactant depletion effects. The important role of the nanoceria shape is first seen in the 40% increase in rate (per g catalyst) comparing the rates (FIG. 17A) of the spherical nanoceria to that of the rod-shaped nanoceria; the cubes presented a much slower rate. Normalization of rates by the SSA yielded a shape-dependent trend (FIG. 7B), which indicates that SSA is not the sole contributing factor to overall activity. If, however, the preferred crystal termination is considered, a trend begins to emerge. It is found that the reaction is 190% faster on the (110) surface than the (111) surface, and ~90% faster on the (100) surface than the (111) surface. This is in agreement with the theoretical prediction that the relative activity of the surface planes are in the order (110) to (100) to (111).

Although nanoceria was explicitly discussed in much of the preceding text the principle and method described may be applied to other metal oxide catalysts having coupled redox oxidation states.

Thus, based on the analysis and discovery described in the foregoing paragraphs, the inventors have discovered a method to predict the catalytic activity of a nanoceria sample. However, the method is equally applicable to any metal oxide wherein the magnetic susceptibility is sensitive to a redox transformation of a diamagnetic oxidation state and a paramagnetic oxidation state, which allows study of the evolution of oxygen vacancies and migration of oxygen atoms from inside the metal oxide structure to its surfaces.

Thus, a first embodiment of this application includes a method to predict the catalytic activity of a metal oxide of formula $M_xO_y$, where x is a number from 1 to 3 and y is a number from 1 to 8. The metal of the metal oxide has redox coupled oxidation states wherein the redox transformation is between oxidation states selected from the group consisting of a diamagnetic oxidation state ($M^{d+}$) and a paramagnetic oxidation state ($M^{p+}$), a paramagnetic oxidation state ($M^{p+}$) and a ferromagnetic oxidation state ($M^{f+}$), and a paramagnetic oxidation state ($M^{p+}$) and an antiferromagnetic oxidation state ($M^{a+}$) where d, p, f and a are independently numbers from 1 to 6 and one of the oxidation states ($M^{d+}$), ($M^{p+}$), ($M^{f+}$), and ($M^{a+}$) is formed by reduction by the $O^{2-}$. Any one of the oxidation states ($M^{d+}$), ($M^{p+}$), ($M^{f+}$), and ($M^{a+}$) may be the ion specie formed by reduction by the $O^{2-}$. The method comprises:

measuring the magnetic susceptibility of a metal oxide sample in an oxygen environment at a specified temperature;

correlating the magnetic susceptibility measured to a value of number of ($M^{d+}$ or $M^{p+}$ or $M^{f+}$ or $M^{a+}$)/g ($O_2$ rich)

measuring the magnetic susceptibility of the metal oxide sample in an oxygen free environment at the specified temperature;

correlating the magnetic susceptibility measured to a value of number of ($M^{d+}$ or $M^{p+}$ or $M^{f+}$ or $M^{a+}$)/g ($O_2$ deficient)

determining the catalytic active ($M^{d+}$ or $M^{p+}$ or $M^{f+}$ or $M^{a+}$) concentration according to the equation:

($M^{d+}$ or $M^{p+}$ or $M^{f+}$ or $M^{a+}$)/g (active)=[($M^{d+}$ or $M^{p+}$ or $M^{f+}$ or $M^{a+}$)/g ($O_2$ deficient)−($M^{d+}$ or $M^{p+}$ or $M^{f+}$ or $M^{a+}$)/g ($O_2$ rich)]/($M^{d+}$ or $M^{p+}$ or $M^{f+}$ or $M^{a+}$)/g ($O_2$ deficient); and predicting catalytic activity of the metal oxide sample with the ($M^{d+}$ or $M^{p+}$ or $M^{f+}$ or $M^{a+}$)/g (active) value.

In a special aspect of the first embodiment a method to predict the catalytic activity of a nanoceria sample is provided. The method comprises:

measuring the magnetic susceptibility of a nanoceria sample in an oxygen environment at a specified temperature;

correlating the magnetic susceptibility measured to a value of number of $Ce^{3+}$/g ($O_2$ rich) measuring the magnetic susceptibility of the nanoceria in an oxygen free environment at the specified temperature;

correlating the magnetic susceptibility measured to a value of number of $Ce^{3+}$/g ($O_2$ deficient)

determining the catalytic active $Ce^{3+}$ concentration according to the equation:

$$Ce^{3+}/g \text{ (active)} = [Ce^{3+}/g \text{ ($O_2$ deficient)} - Ce^{3+}/g \text{ ($O_2$ rich)}]/Ce^{3+}/g \text{ ($O_2$ deficient)}; \text{ and}$$

predicting catalytic activity of the nanoceria with the $Ce^{3+}$/g (active) value.

In one aspect of the above embodiments, the catalytic activity is for the reduction of NO with CO.

Example

The catalytic activity in a generic catalyst system: γ-alumina-supported ceria, $CeO_x$/γ-$Al_2O_3$ was evaluated according to the method described in the embodiment of this application. In addition to bulk ceria, ceria is often used as a component in mixed oxides or as small domains supported on a nominally inert carrier. Multiple reports[31-33] demonstrate that the ceria in these materials remains redox active, but understanding the origins of ceria's activity presents significant challenges. Because the total oxide surface is a mixture of active ceria and inactive support, and because the ceria may not be present as large, crystallographically well-defined phases, reactivity does not easily scale with surface area or a particular surface termination. The method described in the embodiments was applied as follows.

Figure 7B:
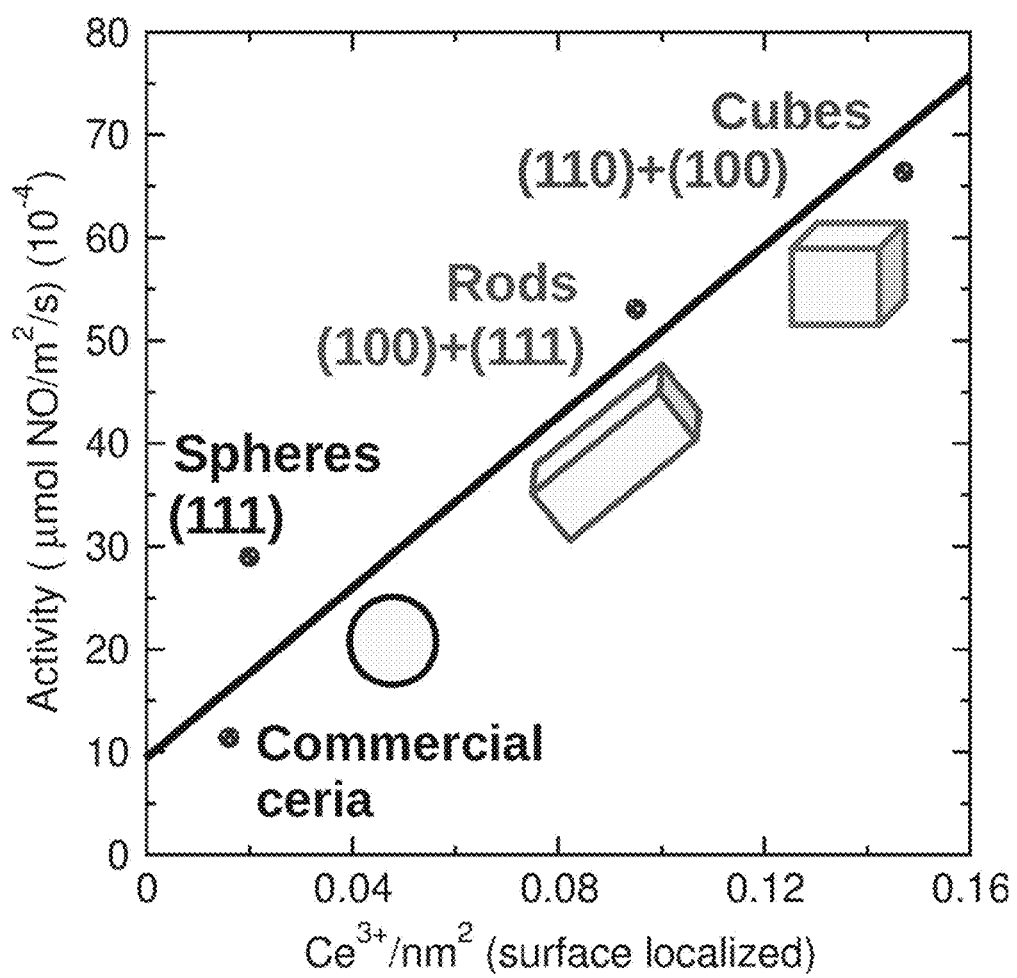
FIG. 7(B) shows surface area normalized NO reduction activity as a function of the surface density of $Ce^{3+}$ sites determined by magnetic susceptibility analysis in $O_2$ deficient conditions for the ceria nanoshapes.
Figure 8A:
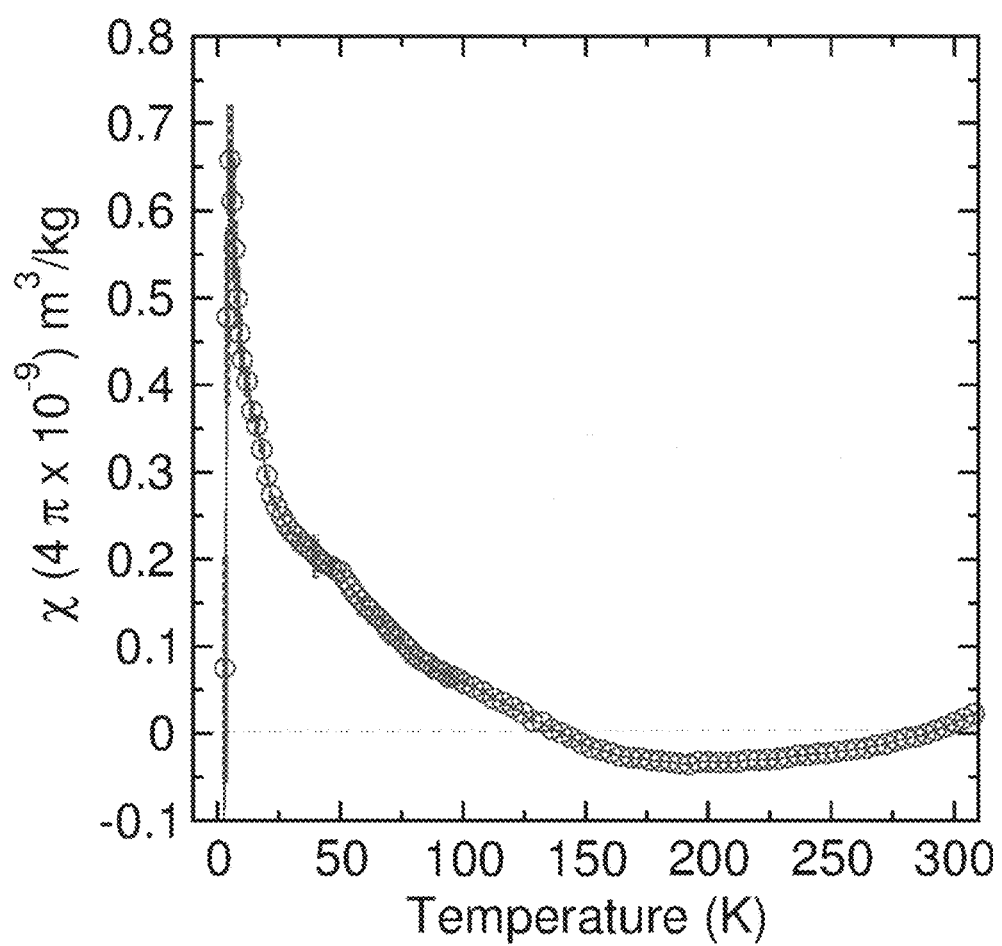
FIG. 8(A) shows the magnetic susceptibility $\chi(T)$ of a 21.1 wt % Ce on $\gamma$-$Al_2O_3$ under $O_2$ rich conditions.
Figure 8B:
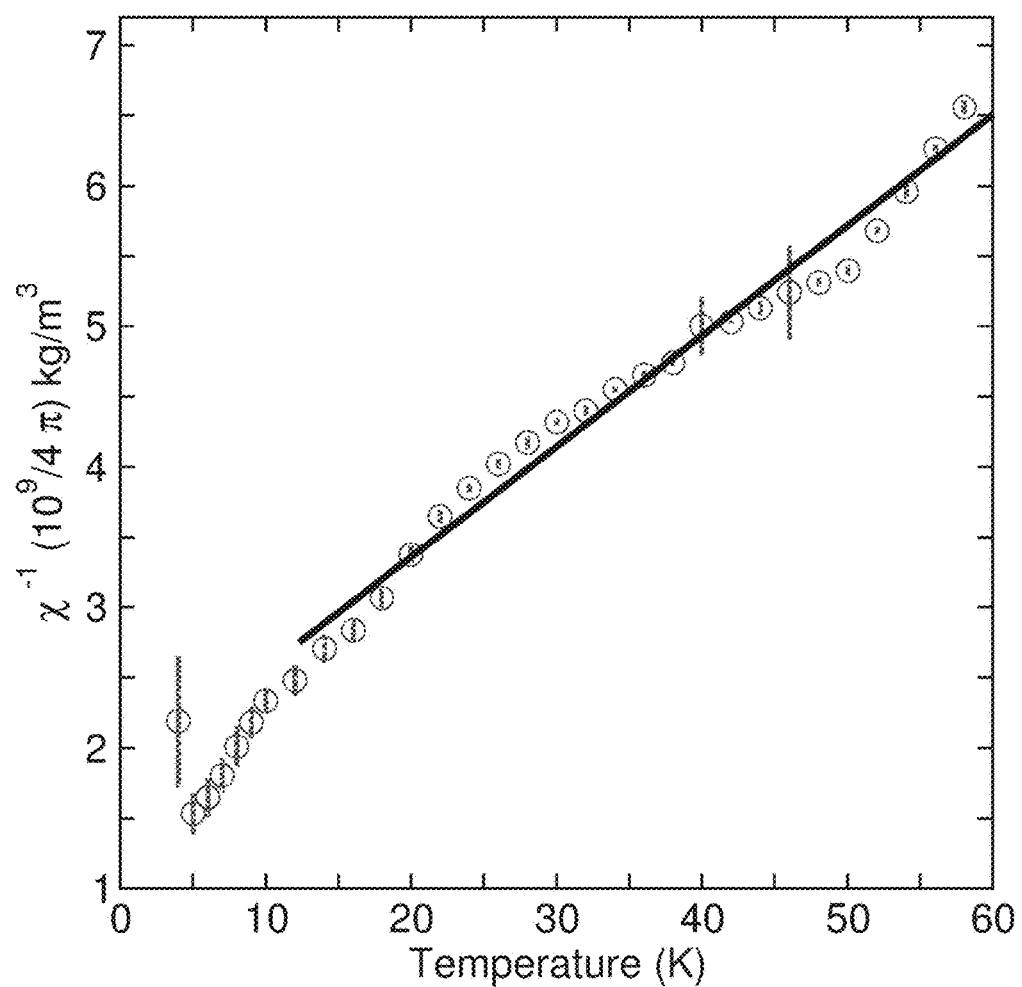
FIG. 8(B) shows the temperature dependence of the inverse magnetic susceptibility $\chi(T)^{-1}$ of a 21.1 wt % Ce on $\gamma$-$Al_2O_3$ under $O_2$ rich conditions.
Figure 8C:
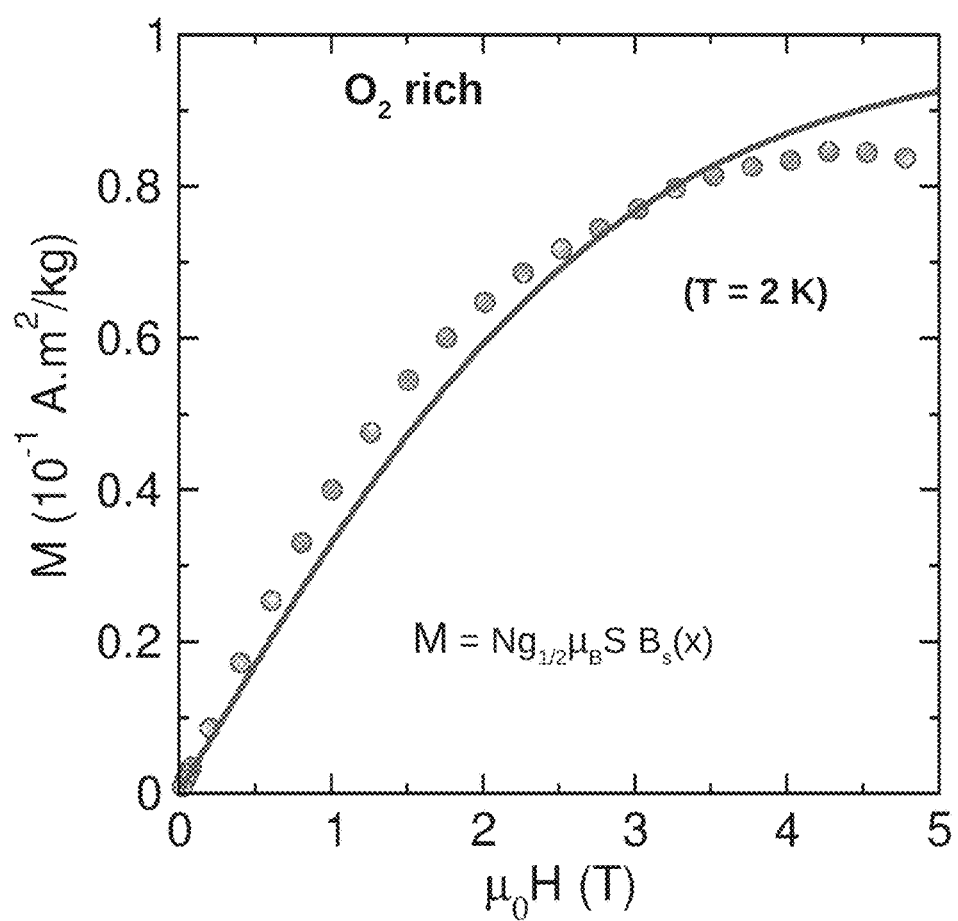
FIG. 8(C) shows the M vs $\mu_0$H data at 2 K with Brillouin function fit for the 21.1 wt % Ce on $\gamma$-$Al_2O_3$ under $O_2$ rich conditions.
Figure 8D:
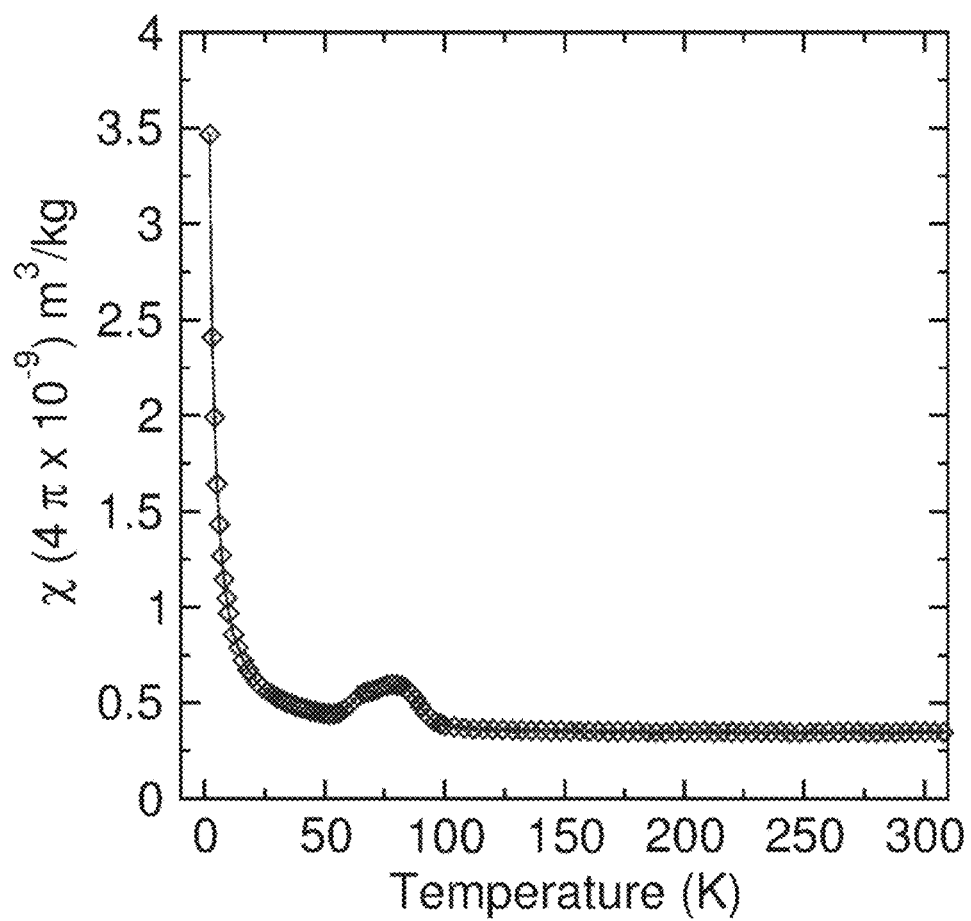
FIG. 8(D) shows the magnetic susceptibility $\chi(T)$ of a 21.1 wt % Ce on $\gamma$-$Al_2O_3$ under $O_2$ deficient conditions.
Figure 8E:
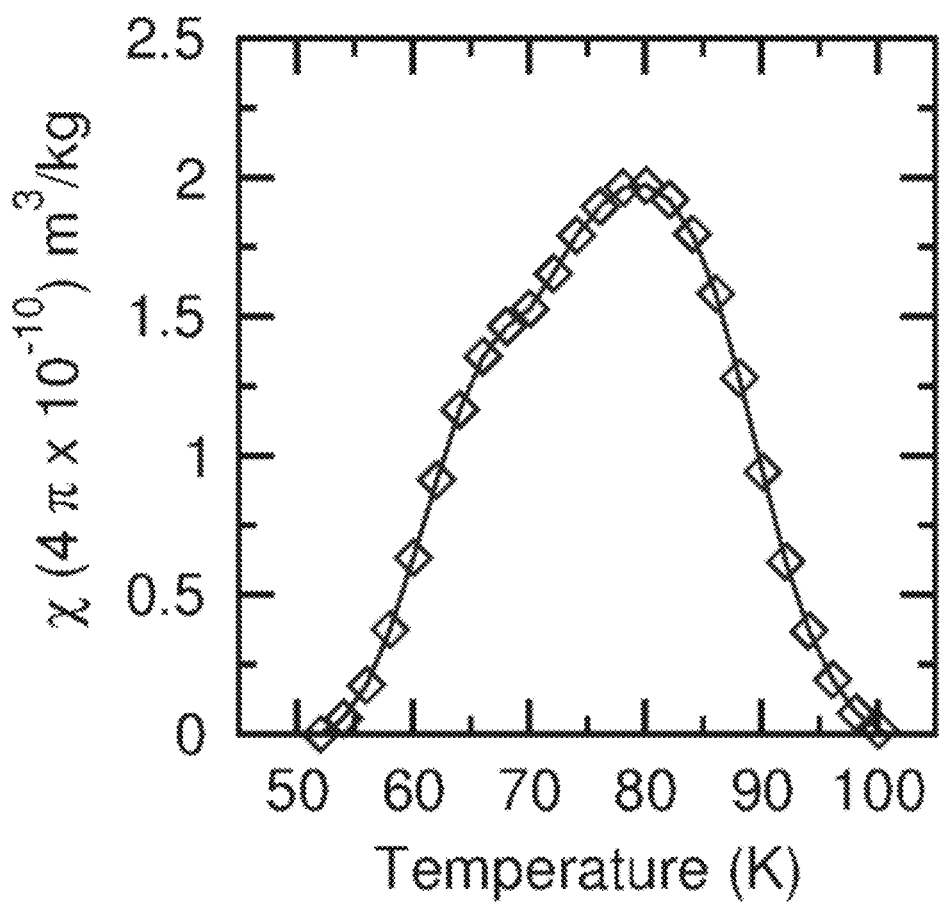
FIG. 8(E) shows the temperature dependence of the inverse magnetic susceptibility $\chi(T)^{-1}$ of a 21.1 wt % Ce on $\gamma$-$Al_2O_3$ under $O_2$ deficient conditions.
Figure 8F:
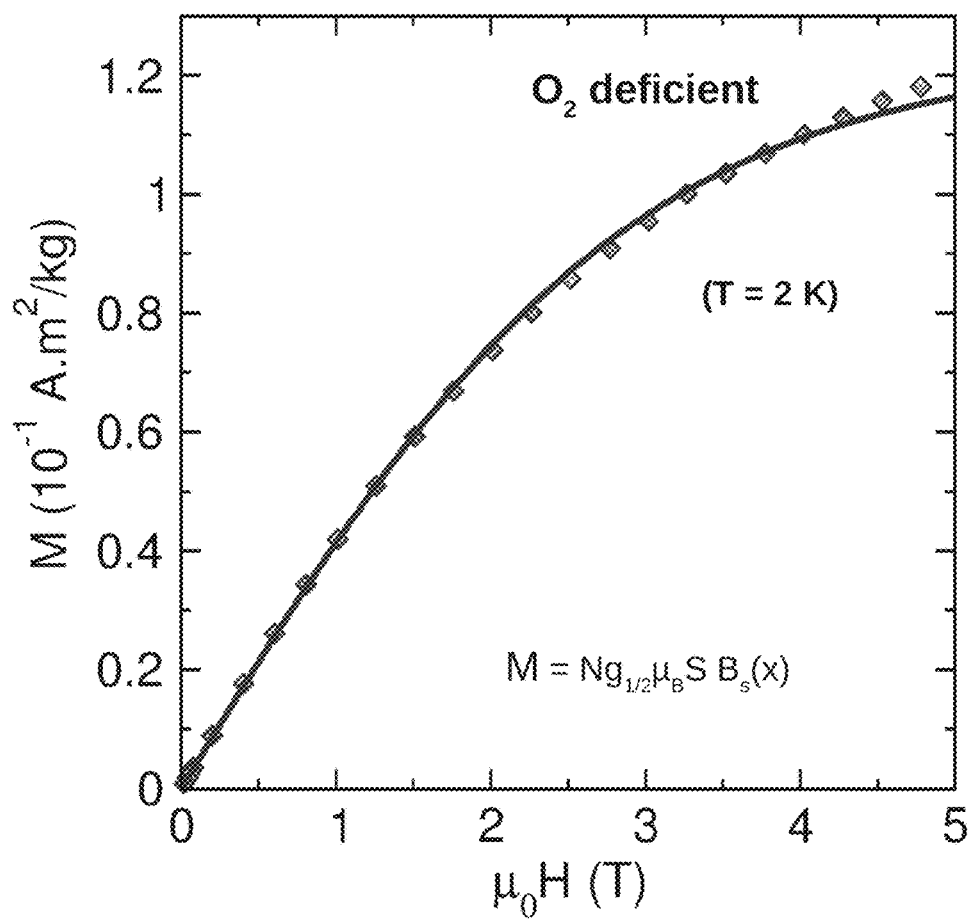
FIG. 8(F) shows the M vs $\mu_0$H data at 2 K with Brillouin function fit for the 21.1 wt % Ce on $\gamma$-$Al_2O_3$ under $O_2$ deficient conditions.
Figure 9:
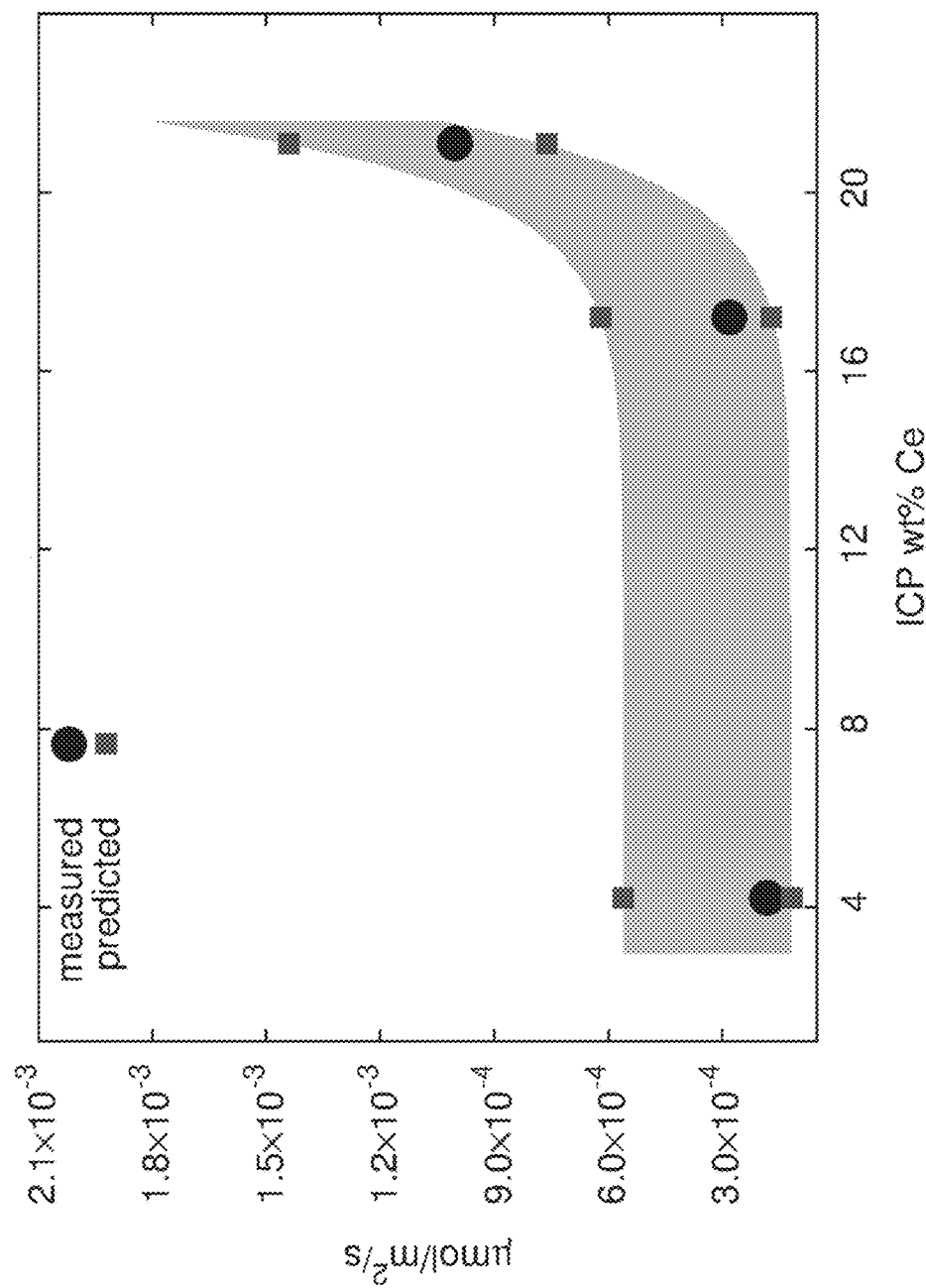
FIG. 9 shows a comparison between predicted and experimentally obtained surface area normalized NO reduction activity at 350° C. over CeOx/$\gamma$-$Al_2O_3$ catalysts with various Ce wt % loadings.
Figure 10:
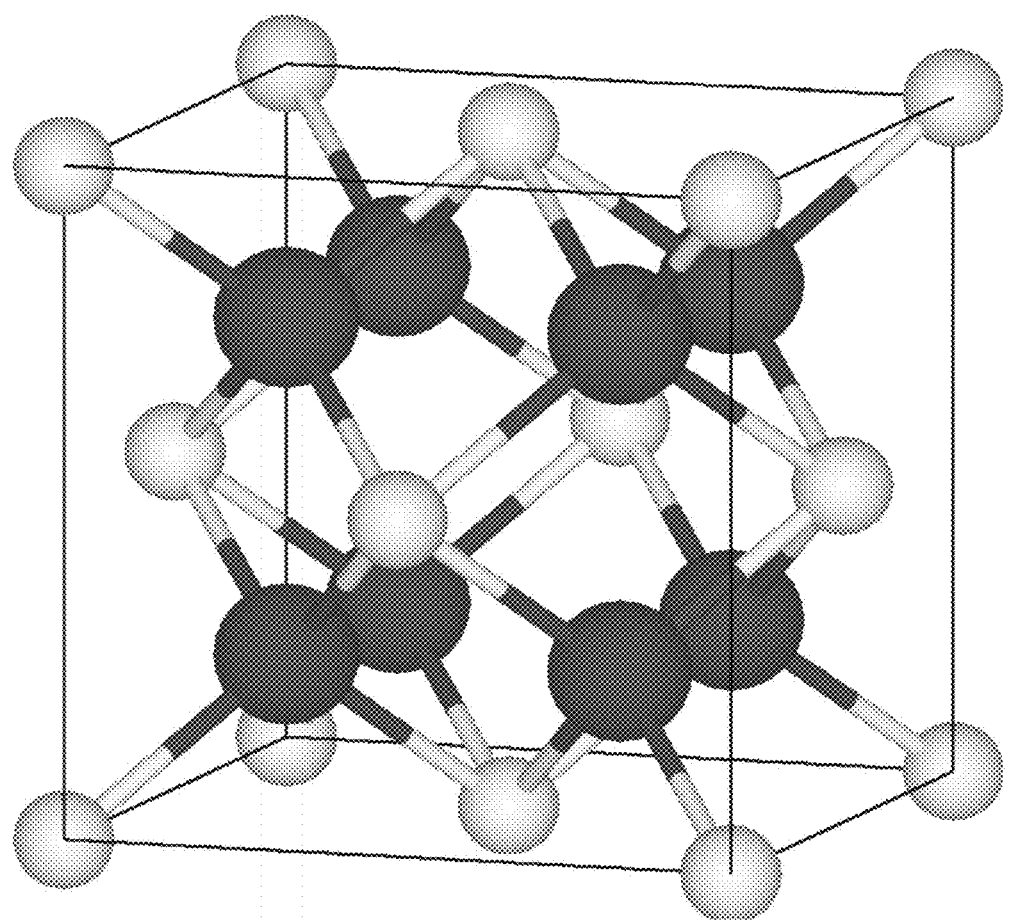
FIG. 10 shows a schematic drawing of the $CeO_2$ unit cell structure.
Figure 18:
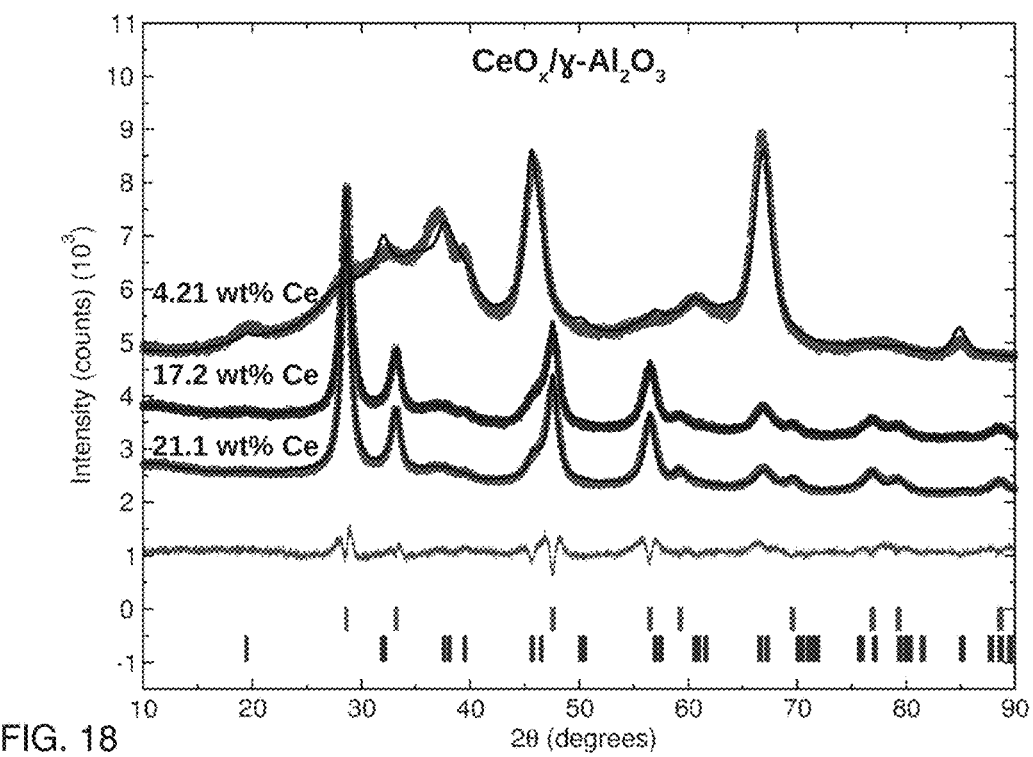
FIG. 18 shows room temperature XRD patterns and refinements of the of $CeO_x$/$\gamma$-$Al_2O_3$ catalyst samples with 4.21, 17.2, and 21.1 wt % Ce loading.
Figure 19:
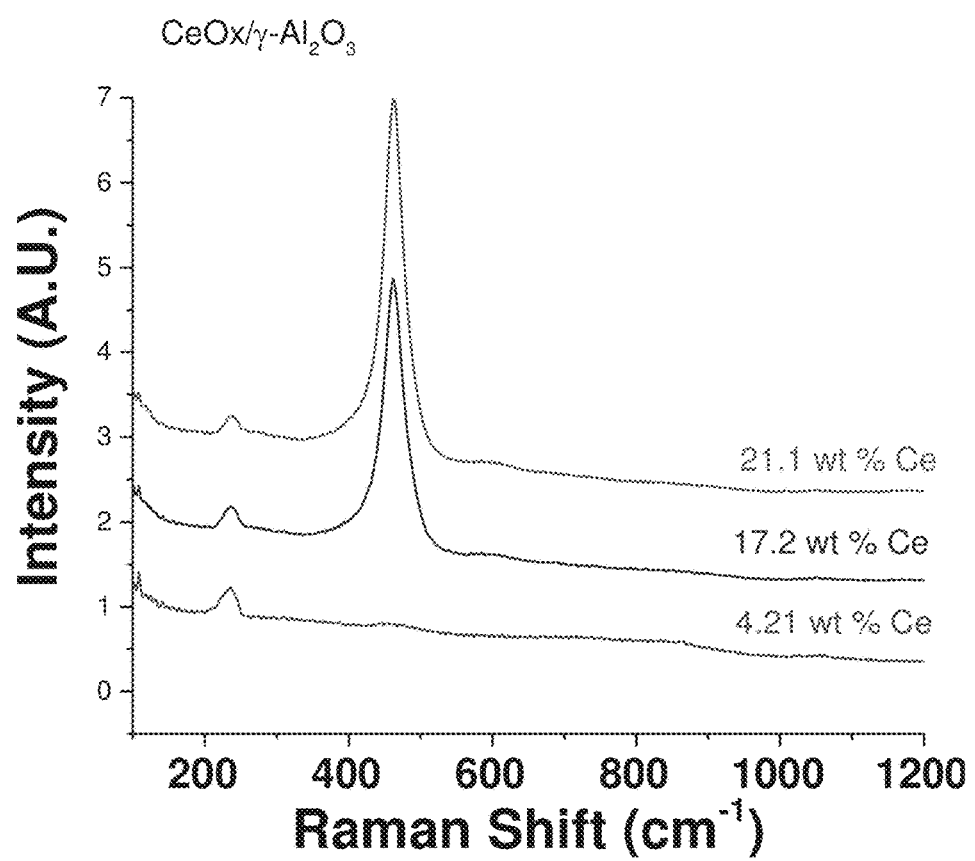
FIG. 19 shows room temperature Raman spectra of the of $CeO_x$/$\gamma$-$Al_2O_3$ catalyst samples with 4.21, 17.2, and 21.1 wt % Ce loading.

Three $CeO_x$/γ-$Al_2O_3$ were prepared with Ce loading verified by ICP analysis as 4.21, 17.2, and 21.1 wt % Ce. X-ray diffraction experiments under ambient conditions were performed followed by full refinements using Full-prof[54] to determine the phase fraction, lattice constants and crystalline sizes (FIG. 18). XRD patterns clearly showed that the 4.21 wt % Ce sample was composed of γ-$Al_2O_3$ (tetragonal I41/amd structure), and the 17.2 and 21.1 wt % Ce are composed of up to 20% γ-$Al_2O_3$ and 80% $CeO_2$ structures, by phase. This structural analysis is consistent with the Raman spectra that clearly identified the F2g vibration of the fluorite $CeO_2$ at 465 cm−1 in the 17.2 wt % and 21.1 wt % $CeO_x$/γ-$Al_2O_3$ systems (FIG. 19). Magnetic susceptibility measurements were performed in $O_2$ rich and deficient environments to estimate the number of $Ce^{3+}$ ions. FIGS. 8A, 8D and 8E a shows typical magnetometry of the 21.1 wt % $CeO_x$/γ-$Al_2O_3$ catalyst with the low temperature transition in susceptibility and FIGS. 8B and 8E shows the data and fit (solid line) to the $\chi^{-1}$ vs T. M($\mu_0$H) below 2 K was poorly fit by a Brillouin function with S=½, and furthermore, was consistent with the observation that the sample undergoes an antiferromagnetic transition. The numbers of $Ce^{3+}$/g in the $O_2$ rich and deficient environments are obtained after subtracting the background contribution of γ-$Al_2O_3$, and FIG. 8A shows the data and fits to susceptibility to quantify the $Ce^{3+}$/g. Similarly, the $O_2$ deficient system presented no antiferromagnetism and the antiferro-to-paramagnetic $O_2$ transition, as shown by the broad maxima between 50 and 100 K (FIG. 8D) as observed for the ceria nanoshapes. Note the magnitude of the transition is ten times smaller than that of nanoshapes, suggesting that the redox ions of $CeO_x$/γ-$Al_2O_3$ are considerably fewer than the nanoshapes—suggesting significantly lower NO activities. As with the nanoshape analysis, the available excess $Ce^{3+}$ ions were obtained from the oxygen deficient $\chi_{FC-ZFC}$(T) scans. Considering the important correlation between the surface localized $Ce^{3+}$ and specific surface area normalized activity, we were able to predict the catalytic activity of the $CeO_x$/γ-$Al_2O_3$ catalysts for the steady-state reduction of CO by NO at 350° C. In order to predict the activities, the surface localized $Ce^{3+}$/nm² were identified by two different methods: Total $Ce^{3+}$ present, and the excess $Ce^{3+}$. These analyses as described later, present bounds that are in excellent agreement to the measured activities. The surface normalized activities of $CeO_x$/γ-$Al_2O_3$ were predicted from a straight line fit of the parameters of the activity vs $Ce^{3+}$/nm² of the ceria shapes (FIG. 7B). The nanoceria shapes intercept that is non-zero essentially identified the bulk ceria base activity. It is important to note that the intercept was taken to be zero for the $CeO_x$/γ-$Al_2O_3$ activity predictions as it identifies the intrinsic activity of the γ-$Al_2O_3$ support (consistent with our measured γ-$Al_2O_3$ activity and results in the literature[35]. A comparison between the experimental activities and the calculated activity predictions are presented in FIG. 9. Our observation indicated that knowing the surface localized excess $Ce^{3+}$ released under the $O_2$ deficient conditions is the key parameter to design efficient NO reduction ceria based catalysts. Once again, these results proved the potential utility of this relationship to design and screen new materials with improved activity. In addition, the non-obvious finding that a dispersed $CeO_2$ catalyst on a high surface area support has lower activity than the bulk $CeO_2$ nanoshapes delivered previously unknown insight into the role of both the surface and bulk of this catalytically interesting material.

Materials and Methods

Synthesis of $CeO_2$ nanoshapes and $CeO_x$/γ-$Al_2O_3$ nanoparticles. All reagents were obtained from Sigma-Aldrich and used as received. Water was purified to 18 M Ω-cm resistivity by a Barnstead NanoPure system.

Ceria nanocubes were synthesized following a previously reported method[13, 36]. 2.0 mmol of Ce(NO$_3$)$_3$6H$_2$O was dissolved in 5 mL water, mixed with 35 mL of 5 M NaOH, and stirred in a Teflon container for 30 minutes. The Teflon container was put in a stainless steel autoclave and heated for 24 h at 180° C. in an electric oven. The snow-white solids was separated by centrifuge and washed with alternating water and ethanol three times. Nanocubes were dried overnight at 70° C. in air. Their color remained white after drying. Total yield was 0.26 g (76%).

The synthesis of ceria nanorods was based on a previously reported microwave hydrothermal method[37]. 41.9 mmol of cerium (III) nitrate hexahydrate (Ce(NO$_3$)$_3$6H$_2$O, 99.9% purity) was dissolved in 105 mL water, the solution mixed with 105 mL of 5 M sodium hydroxide (NaOH), stirred for 30 minutes, and split evenly into four Teflon containers. The containers were heated in a Milestone EthosEZ Microwave at 10° C./min to 160° C., held at 160° C. for 1 hour, and cooled to room temperature. A light purple solid was separated by centrifuge and washed with alternating water and ethanol three times. Nanorods were dried overnight at 70° C. in air, and became yellow after drying. Total yield was 7.07 g (98% yield).

The synthesis of ceria nanospheres was based on a previously reported microwave hydrothermal method[37,38]

5.0 mmol of cerium (IV) ammonium nitrate $((NH_4)_2Ce(NO_3)_6$ 98.5% purity) was dissolved in 25 mL water, mixed with 25 mL of 5 M NaOH in a Teflon container and stirred for 3 hours. The container was heated in a Milestone EthosEZ Microwave at 10° C./min to 100° C., held at 100° C. for 10 minutes, and cooled to room temperature. The creamy yellow solids were separated by centrifuge and washed with alternating DI water and ethanol three times. Nanospheres were dried at 70° C. in air overnight, and stayed light yellow after drying. Total yield was 0.91 g (106% yield, indicating a small amount of retained surface water or ethanol, as expected from the high surface areas).

Three alumina-supported cerium oxide catalysts ($CeO_x$/γ-$Al_2O_3$) of differing Ce loading were prepared by incipient wetness impregnation of aqueous solutions of $Ce(NO_3)_3 \cdot 6H_2O$ of varying concentrations onto a γ-$Al_2O_3$ support (BET SSA=209 $m^2$/g). After impregnation, the samples were dried at 120° C. (1° C./min) for 24 hrs., followed by calcination in air at 500° C. (2° C./min) for 30 min. The final Ce loadings on the γ-$Al_2O_3$ support were determined by ICP to be 4.21, 17.2 and 21.1 Ce wt %.

Transmission Electron Microscopy.

TEM images and electron diffraction data was collected at the EPIC facility of the NUANCE Center at Northwestern University using the JEOL-2100F (0.16 nm resolution and 0.92 eV energy resolution). Catalysts were dispersed in ethanol and sonicated for 30 min. The resulting suspension was pipetted on to a holey carbon grid and dried overnight at room temperature. TEM and electron diffraction data were taken at 200 kV accelerating voltage, 140 A emission and 0.5 angstrom probe size. Electron diffraction parameters were determined using the Digital Micrograph program.

X-Ray Powder Diffraction.

X-ray powder diffraction patterns were collected using a Bruker D8 Davinci with Cu K radiation using Bragg-Brentano geometry under ambient conditions. The diffraction patterns were collected on dried nanoparticle samples with a knife edge above the sample on a zero-background quartz slides.

Brunauer-Emmett-Teller Analysis.

$N_2$ physisorption isotherms were obtained using a Micromeritics ASAP 2010 instrument. Using the BET equation, $N_2$ physisorption isotherms were utilized to determine specific surface areas (58). Before measurements, all materials were degassed 12 h at <5 mTorr and 150° C.

Activity Measurements.

Steady-state catalytic activities were measured using a fixed bed quartz tubular reactor with temperature and gas flow control. The reactor was loaded with 50 mg of catalyst powder that was mixed with quartz sand as a diluent in order to achieve a constant gas hourly space velocity (GHSV) of approximately 15,000 $hr^{-1}$. The catalyst was first pretreated n 30 sccm of 10% $O_2$/He at 500° C. for 30 min, and then cooled in flowing UHP He. The reduction of NO by CO was monitored at 300° C. and 350° C. for 45 min each at a total flow rate of 100 sccm with a stoichiometric composition of 4000 ppm NO, 4000 ppm CO, 8000 ppm Ar, and He balance. Mass spectrometry of the gas phase product stream was obtained continuously using a quadrupole mass spectrometer (MKS Instruments, Inc. Cirrus-2). The Ar present in the reactant stream acted as tracer of constant concentration and the Ar signal at m/z=40 was used to normalize each of the mass spectrum traces. The 100% and 0% conversion of NO was defined as the normalized mass spectrum intensity at m/z=30 under inert flow, and under NO+CO reaction mixture flow while bypassing the reactor, respectively. Linear interpolation determined the resulting NO conversions at steadystate temperatures. Rates (mol NO/s) at 350° C. were calculated from differential NO conversions (15%). Mass-normalized activity (mol NO/g/s) and SSA-normalized activity (mol NO/$m^2$/s) were calculated using the mass of catalyst and the BET-determined SSA, respectively.

Magnetic Measurements.

Figure 12:
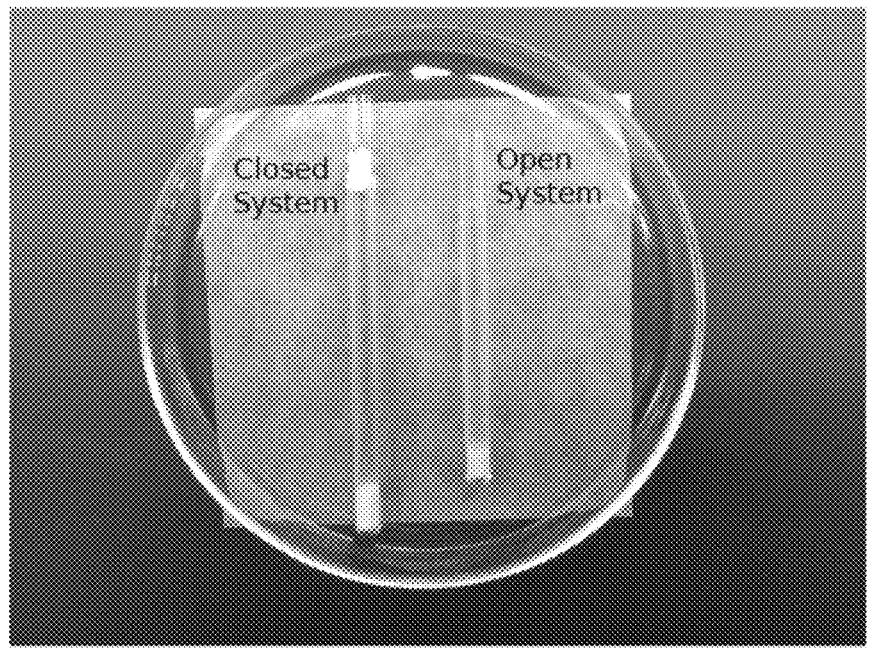
FIG. 12 shows an image of the sample tube preparation for magnetic susceptibility measurements under a closed (oxygen rich) or open (oxygen deficient) environment.
Figure 13:
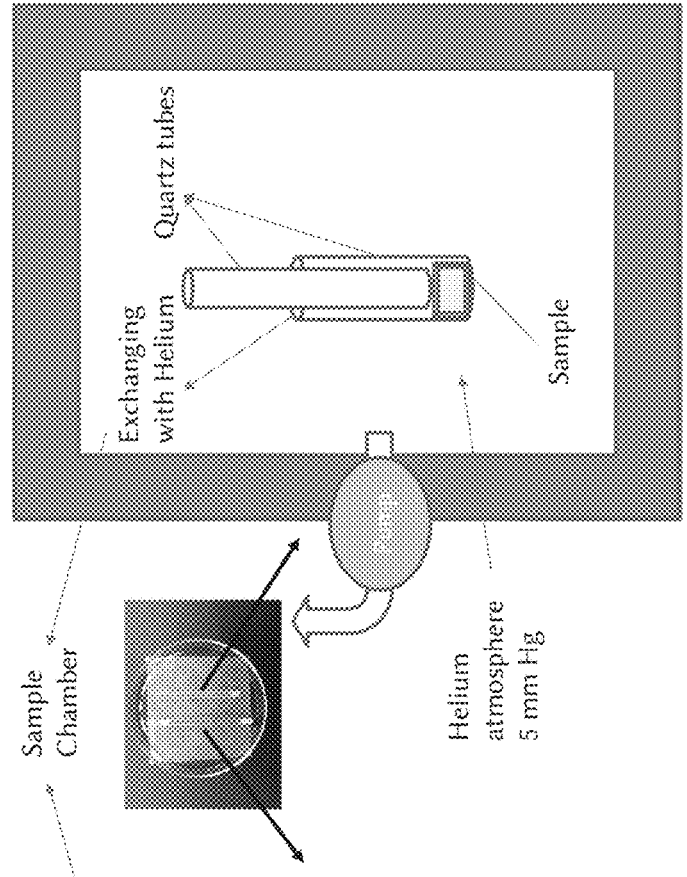
FIG. 13 shows the schematic diagram showing the oxygen rich and oxygen deficient environment experimental setup for magnetic susceptibility measurements.
Figure 13:
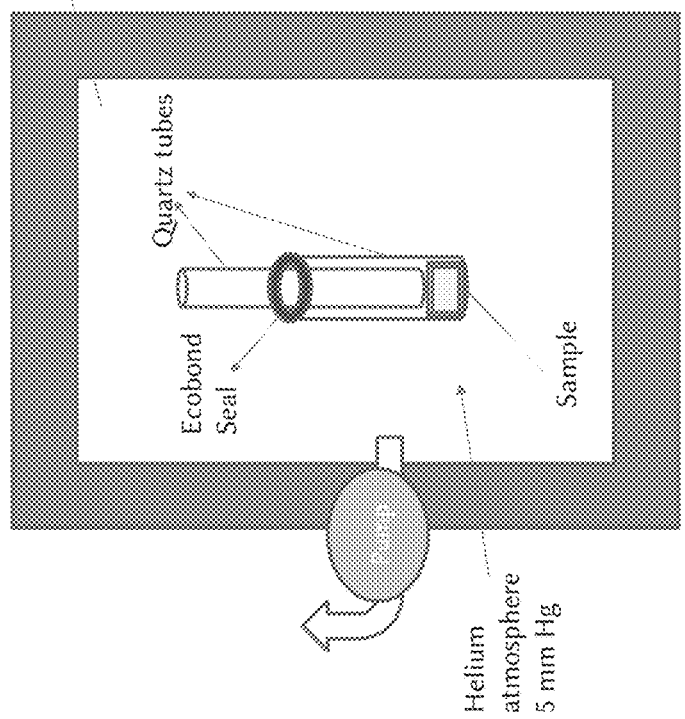

Magnetometry experiments were performed using a Quantum Design magnetic properties measurement system (MPMS XL-5 using the Reciprocating Sample Option (RSO)). The samples were mounted in low background NMR (Norell high resolution S-5-20-8) tubes. DC susceptibility measurements were done using a 10 mT applied field. Experiments under oxygen rich conditions were carried out in sealed tubes at approximately 160 Torr $O_2$, while oxygen poor experiments were carried out under dynamic pumping to achieve an 5 Torr He atmosphere (see FIGS. 12 and 13). During each magnetic measurement the temperature was held at a fixed set point. NMR tubes are sensitive to thermal gradients, so during the temperature scan between measurements a scan rate of 1 K $min^{-1}$ below 100 K and 2 K $min^{-1}$ above that was used during heating and cooling.

Raman Measurements.

Raman spectra were collected with a Horiba-Jobin Yvon Labram HR high-resolution Raman microscope instrument equipped a 532 nm light laser source (Laser Quantum Ventus 532 Dedicated Raman Laser, diode pumped) and a back-illuminated CCD detector (Horiba-Jobin Yvon Synapse 1024 1 256). The spectrometer was optimized to a spectral resolution of 2 cm☐1 using a 600 grooves/mm grating. The Rayleigh scattered light was rejected with holographic notch filters.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

REFERENCES

1. Liu, X., Zhou, K., Wang, L., Wang, B. & Li, Y. Oxygen vacancy clusters promoting reducibility and activity of ceria nanorods. *J. Am. Chem. Soc.* 131, 3140-3141 (2009).
2. Esch, F. et al. Electron Localization Determines Defect Formation on Ceria Substrates. *Science* (80-.). 309, 752-5 (2005).
3. Campbell, C. T. & Peden, C. H. F. Oxygen Vacancies and Catalysis on Ceria Surfaces. *Science* (80-.). 309, (2005).
4. Zhang, F., Wang, P., Koberstein, J., Khalid, S. & Chan, S. W. Cerium oxidation state in ceria nanoparticles studied with X-ray photoelectron spectroscopy and absorption near edge spectroscopy. *Surf. Sci.* 563, 74-82 (2004).
5. Zotin, F. M. Z., Tournayan, L., Varloud, J., Perrichon, V. & Fréty, R. Temperature-programmed reduction: limitation of the technique for determining the extent of reduction of either pure ceria or ceria modified by additiv. *Appl. Catal. A Gen.* 98, 99-114 (1993).
6. Mamontov, E. & Egami, T. Structural defects in a nanoscale powder of CeO2 studied by pulsed neutron diffraction. *J. Phys. Chem. Solids* 61, 1345-1356 (2000).

7. Laachir, A. et al. Reduction of CeO 2 by hydrogen. Magnetic susceptibility and Fourier-transform infrared, ultraviolet and X-ray photoelectron spectroscopy measurements. *J. Chem. Soc., Faraday Trans.* 87, 1601-1609 (1991).
8. Dutta, P. et al. Concentration of $Ce^{3+}$ and Oxygen Vacancies in Cerium Oxide Nanoparticles. *Chem. Mater.* 18, 5144-5146 (2006).
9. Skorodumova, N., Baudin, M. & Hermansson, K. Surface properties of CeO2 from first principles. *Phys. Rev. B* 69, 1-8 (2004).
10. Huang, W. & Gao, Y. Morphology-dependent surface chemistry and catalysis of CeO 2 nanocrystals. *Catal. Sci. Technol.* 4, 3772-3784 (2014).
11. Nolan, M., Grigoleit, S., Sayle, D. C., Parker, S. C. & Watson, G. W. Density functional theory studies of the structure and electronic structure of pure and defective low index surfaces of ceria. *Surf Sci.* 576, 217-229 (2005).
12. Ganduglia-Pirovano, M. V., Hofmann, A. & Sauer, J. Oxygen vacancies in transition metal and rare earth oxides: Current state of understanding and remaining challenges. *Surf Sci. Rep.* 62, 219-270 (2007).
13. Mai, H. X. et al. Shape-selective synthesis and oxygen storage behavior of ceria nanopolyhedra, nanorods, and nanocubes. *J. Phys. Chem. B* 109, 24380-24385 (2005).
14. Yang, S. & and Lian Gao. Controlled Synthesis and Self-Assembly of {CeO_2}Nanocubes. *J. Am. Chem. Soc.* 128, 9330-9331 (2006).
15. Lin, Y., Wu, Z., Wen, J., Poeppelmeier, K. R. & Marks, L. D. Imaging the Atomic Surface Structures of $CeO_2$ Nanoparticles. *Nano Lett.* 14, 191-196 (2014).
16. Agarwal, S. et al. Exposed Surfaces on Shape-Controlled Ceria Nanoparticles Revealed through AC-TEM and Water-Gas Shift Reactivity. *Chem Sus Chem* 6, 1898-1906 (2013).
17. Toby, B. H., IUCr & D., B. I. EXPGUI, a graphical user interface for GSAS. *J. Appl. Crystallogr.* 34, 210-213 (2001).
18. Lawrence, J. Speculations on the critical behavior of reduced moment antiferromagnetic cerium compounds (invited). *J. Appl. Phys.* 53, 2117-2121 (1982).
19. Elliott, R. J. & Stevens, K. W. H. A Preliminary Survey of the Paramagnetic Resonance Phenomena observed in Rare Earth Ethyl Sulphates. *Proc. Phys. Soc. Sect. A* 64, 205-207 (1951).
20. Bogle, G. S., Cooke, A. H. & Whitley, S. Paramagnetism of Cerium Ethylsulphate at Low Temperatures. *Proc. Phys. Soc. Sect. A* 64, 931-932 (1951).
21. Das, I. & Sampathkumaran, E. V. Magnetic ordering in Ce2RhSi3. *J. Magn. Magn. Mater.* 137, L239-L242 (1994).
22. Kase, N., Muranaka, T. & Akimitsu, J. Antiferromagnetic Kondo-lattice system with moderate heavy-fermion behavior. *J. Magn. Magn. Mater.* 321, 3380-3383 (2009).
23. DeFotis, G. C. Magnetism of solid oxygen. *Phys. Rev. B* 23, 4714-4740 (1981).
24. Gregory, S. Adsorbed Oxygen as an Amorphous Antiferromagnetic System. *Phys. Rev. Lett.* 39, 1035-1038 (1977).
25. Awschalom, D. D., Lewis, G. N. & Gregory, S. Melting and Wetting Behavior in Oxygen Films. *Phys. Rev. Lett.* 51, 586-588 (1983).
26. Köbler, U. & Marx, R. Susceptibility study of physisorbed oxygen layers on graphite. *Phys. Rev. B* 35, 9809-9816 (1987).
27. Murakami, Y. Magnetic and structural phase transitions of physisorbed oxygen layers. *J. Phys. Chem. Solids* 59, 467-485 (1998).
28. TROVARELLI, A. Catalytic Properties of Ceria and $CeO_2$-Containing Materials. *Catal. Rev.* 38, 439-520 (1996).
29. Morrish, A. H. *The Physical Principles of Magnetism.* Wiley-IEEE Press 1, (1965).
30. Trovarelli, A. et al. Nanophase Fluorite-Structured CeO2-ZrO2 Catalysts Prepared by High-Energy Mechanical Milling. *J Catal.* 169, 490-502 (1997).
31. Skala, T., Tsud, N., Prince, K. C. & Matolin, V. Formation of alumina-ceria mixed oxide in model systems. *Appl. Surf Sci.* 257, 3682-3687 (2011).
32. Piras, A. et al. Structural and Morphological Investigation of Ceria-Promoted Al2O3 under Severe Reducing/Oxidizing Conditions. doi:10.1021/jp0440737
33. Shyu, J. Z., Weber, W. H. & Gandhi, H. S. Surface characterization of alumina-supported ceria. *J. Phys. Chem.* 92, 4964-4970 (1988).
34. Rodriguez-Carvajal, J. Recent advances in magnetic structure determination by neutron powder diffraction. *Phys. B Condens. Matter* 192, 55-69 (1993).
35. Kim, H., Takashima, K. & Katsura, S. Low-temperature NOx reduction processes using combined systems of pulsed corona discharge and catalysts. *J. Phys. D* (2001).
36. Wu, Z., Li, M., Howe, J., Meyer, H. M. & Overbury, S. H. Probing defect sites on CeO2 nanocrystals with well-defined surface planes by raman spectroscopy and O2 adsorption. *Langmuir* 26, 16595-16606 (2010).
37. Arauijo, V. D. et al. $CeO_2$ nanoparticles synthesized by a microwave-assisted hydrothermal method: evolution from nanospheres to nanorods. *Cryst Eng Comm* 14, 1150-1154 (2012).
38. Bonamartini Corradi, A., Bondioli, F., Ferrari, A. M. & Manfredini, T. Synthesis and characterization of nano-sized ceria powders by microwave-hydrothermal method. *Mater. Res. Bull.* 41, 38-44 (2006).

The invention claimed is:

1. A method to predict the catalytic activity of a metal oxide of formula $M_xO_y$, where x is a number from 1 to 3 and y is a number from 1 to 8, the method comprising:

measuring the magnetic susceptibility of a metal oxide sample in an oxygen environment at a specified temperature;

correlating the magnetic susceptibility measured to a value of number of ($M^{d+}$ or $M^{p+}$ or $M^{f+}$ or $M^{a+}$)/g ($O_2$ rich)

measuring the magnetic susceptibility of the metal oxide sample in an oxygen free environment at the specified temperature;

correlating the magnetic susceptibility measured to a value of number of ($M^{d+}$ or $M^{p+}$ or $M^{f+}$ or $M^{a+}$)/g ($O_2$ deficient)

determining the catalytic active ($M^{d+}$ or $M^{p+}$ or $M^{f+}$ or $M^{a+}$) concentration according to the equation:

($M^{d+}$ or $M^{p+}$ or $M^{f+}$ or $M^{a+}$)/g (active)=[($M^{d+}$ or $M^{p+}$ or $M^{f+}$ or $M^{a+}$)/g ($O_2$ deficient)−($M^{d+}$ or $M^{p+}$ or $M^{f+}$ or $M^{a+}$)/g ($O_2$ rich)]/($M^{d+}$ or $M^{p+}$ or $M^{f+}$ or $M^{a+}$)/g ($O_2$ deficient); and predicting catalytic activity of the metal oxide sample with the ($M^{d+}$ or $M^{p+}$ or $M^{f+}$ or $M^{a+}$)/g (active) value;

wherein the metal of the metal oxide has redox coupled oxidation states wherein the redox transformation is between oxidation states selected from the group consisting of a diamagnetic oxidation state ($M^{d+}$) and a paramagnetic oxidation state ($M^{p+}$), a paramagnetic oxidation state ($M^{p+}$) and a ferromagnetic oxidation state ($M^{f+}$), and a paramagnetic oxidation state ($M^{p+}$) and an antiferromagnetic oxidation state ($M^{a+}$) where d, p, f and a are independently numbers from 1 to 6 and one of the oxidation states ($M^{d+}$), ($M^{p+}$), ($M^{f+}$), and ($M^{a+}$) is formed by reduction by the $O^{2-}$.

2. The method of claim 1 wherein the metal M is selected from the group consisting of a transition metal, a lanthanide metal and an actinide metal.

3. A method to predict the catalytic activity of a nanoceria sample, comprising:

measuring the magnetic susceptibility of a nanoceria sample in an oxygen environment at specified temperature;

correlating the magnetic susceptibility measured to a value of number of $Ce^{3+}/g$ ($O_2$ rich);

measuring the magnetic susceptibility of the nanoceria in an oxygen free environment at the specified temperature;

correlating the magnetic susceptibility measured to a value of number of $Ce^{3+}/g$ ($O_2$ deficient)

determining the catalytic active $Ce^{3+}$ concentration according to the equation:

$$Ce^{3+}/g \text{ (active)} = [Ce^{3+}/g \text{ (}O_2\text{ deficient)} - Ce^{3+}/g \text{ (}O_2 \text{ rich)}]/Ce^{3+}/g \text{ (}O_2 \text{ deficient)}; \text{ and}$$

predicting catalytic activity of the nanoceria with the $Ce^{3+}/g$ (active) value.

4. The method according to claim 3, wherein the catalytic activity is for the reduction of NO with CO.

* * * * *